US009416380B2

(12) United States Patent
Kim et al.

(10) Patent No.: US 9,416,380 B2
(45) Date of Patent: Aug. 16, 2016

(54) YEAST CELL WITH ACTIVATED LACTATE DEHYDROGENASE AND METHOD OF PRODUCING LACTATE USING THE YEAST CELL

(71) Applicant: Samsung Electronics Co., Ltd., Suwon-si, Gyeonggi-do (KR)

(72) Inventors: Sung-soo Kim, Hwaseong-si (KR); So-young Lee, Daegu (KR); Chang-duk Kang, Gwacheon-si (KR); Ju-young Lee, Daegu (KR); Kwang-myung Cho, Seongnam-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 0 days.

(21) Appl. No.: 14/340,362

(22) Filed: Jul. 24, 2014

(65) Prior Publication Data

US 2015/0044740 A1 Feb. 12, 2015

(30) Foreign Application Priority Data

Aug. 9, 2013 (KR) ........................ 10-2013-0094891

(51) Int. Cl.
*C12N 9/04* (2006.01)
*C12N 15/81* (2006.01)
*C12P 7/56* (2006.01)

(52) U.S. Cl.
CPC ................ *C12P 7/56* (2013.01); *C12N 9/0006* (2013.01); *C12Y 101/01027* (2013.01); *C12N 15/81* (2013.01); *Y02P 20/52* (2015.11)

(58) Field of Classification Search
CPC ........ C12N 9/0006; C12N 15/81; C12P 7/56; C12Y 101/010027; C12Y 401/01001
USPC ........................ 435/254.21, 254.11, 139, 189
See application file for complete search history.

(56) References Cited

U.S. PATENT DOCUMENTS 7,229,805 B2 6/2007 Rajgarhia et al.
2004/0029238 A1 * 2/2004 Rajgarhia ................ C12N 1/16 435/139
2009/0239274 A1 * 9/2009 Sawai ....................... C12P 7/56 435/139
2012/0129230 A1 * 5/2012 Suominen ................ C12P 7/56 435/125
2013/0065284 A1 3/2013 Chung et al.

FOREIGN PATENT DOCUMENTS

KR 2013-0001103 A 1/2013
KR 2013-0001121 A 1/2013

OTHER PUBLICATIONS

Devos et al., Proteins: Structure, Function and Genetics, 2000, vol. 41: 98-107.*
Whisstock et al., Quarterly Reviews of Biophysics 2003, vol. 36 (3): 307-340.*
Kisselev L., (Structure, 2002, vol. 10: 8-9.*
Witkowski et al., (Biochemistry 38:11643-11650, 1999.*
Engh et al. Eur. J. Cell Biol. 2010, 89, 864-872.*

* cited by examiner

*Primary Examiner* — Md. Younus Meah
(74) *Attorney, Agent, or Firm* — Leydig, Voit & Mayer, Ltd.

(57) ABSTRACT

A yeast cell comprising LDH from a *Sordaria* genus fungi, in which activity of lactate dehydrogenase converting pyruvate into lactate is increased, as well as a method of preparing the yeast cell and a method of using the yeast cell to produce lactate.

11 Claims, 7 Drawing Sheets

YEAST CELL WITH ACTIVATED LACTATE DEHYDROGENASE AND METHOD OF PRODUCING LACTATE USING THE YEAST CELL

CROSS-REFERENCE TO RELATED APPLICATIONS

This application claims the benefit of Korean Patent Application No. 10-2013-0094891, filed on Aug. 9, 2013, in the Korean Intellectual Property Office, the entire disclosure of which is hereby incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 39,092 Bytes ASCII (Text) file named "716721_ST25.TXT," created on Jul. 24, 2014.

BACKGROUND

1. Field

The present disclosure relates to a yeast cell with an activated lactate dehydrogenase and a method of producing lactate using the yeast cell.

2. Description of the Related Art

Lactate is an organic acid that is broadly used in various industrial fields, such as food, pharmaceutics, chemicals, and electronics. Lactate is colorless, odorless, and a low-volatile material that dissolves well in water. Lactate is non-toxic to the human body and thus may be used as a flavor agent, a taste agent, or a preserving agent. Also, lactate is an environment-friendly alternative polymer material and a raw material of a polylactic acid (PLA), that is, biodegradable plastic.

PLA is a polyester-based resin that is ring-open polymerized by converting it into lactide, which is a dimer, for technical polymerization and may be variously processed into a film, sheet, fiber, plastic, etc. Thus, demands for PLA as bioplastic have recently increased to broadly replace conventional typical petrochemical plastic, such as polyethylene (PE), polypropylene (PP), polyethylene terephthalate (PET), or polystylene (PS).

Lactate includes both a hydroxyl group and a carboxyl group and thus is highly reactive. Accordingly, lactate is easily converted into industrially important compounds, such as lactate ester, acetaldehyde, or propyleneglycol, and thus has received attention as an alternative chemical material of the next generation in chemical industry.

Currently, lactate is produced by an industrially petrochemical synthesis process and a biotechnological fermentation process. The petrochemical synthesis process is performed by oxidizing ethylene derived from crude oil, preparing lactonitrile through addition of hydrogen cyanide after acetaldehyde, purifying by distillation, and hydrolyzing by using chloric acid or phosphoric acid. The biotechnological fermentation process is used to manufacture lactate from a reproducible carbon hydrate, such as, starch, sucrose, maltose, glucose, fructose, or xylose, as a substrate.

Therefore, a strain for efficiently producing lactate and a lactate production method using the strain are needed.

SUMMARY

Provided is a recombinant yeast cell comprising a lactate dehydrogenase (LDH) enzyme from *Sordaria* genus fungi.

Also provided is a method of producing the yeast cell by introducing into a yeast cell a gene encoding an LDH enzyme from a *Sordaria* genus fungi the method comprising introducing into a yeast cell a gene encoding an LDH enzyme from a *Sordaria* genus fungi.

Further provided is a method of producing lactate using the recombinant yeast cell by culturing the recombinant yeast cell in an appropriate medium to produce lactate, and collecting lactate from the culture.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Figure 1:
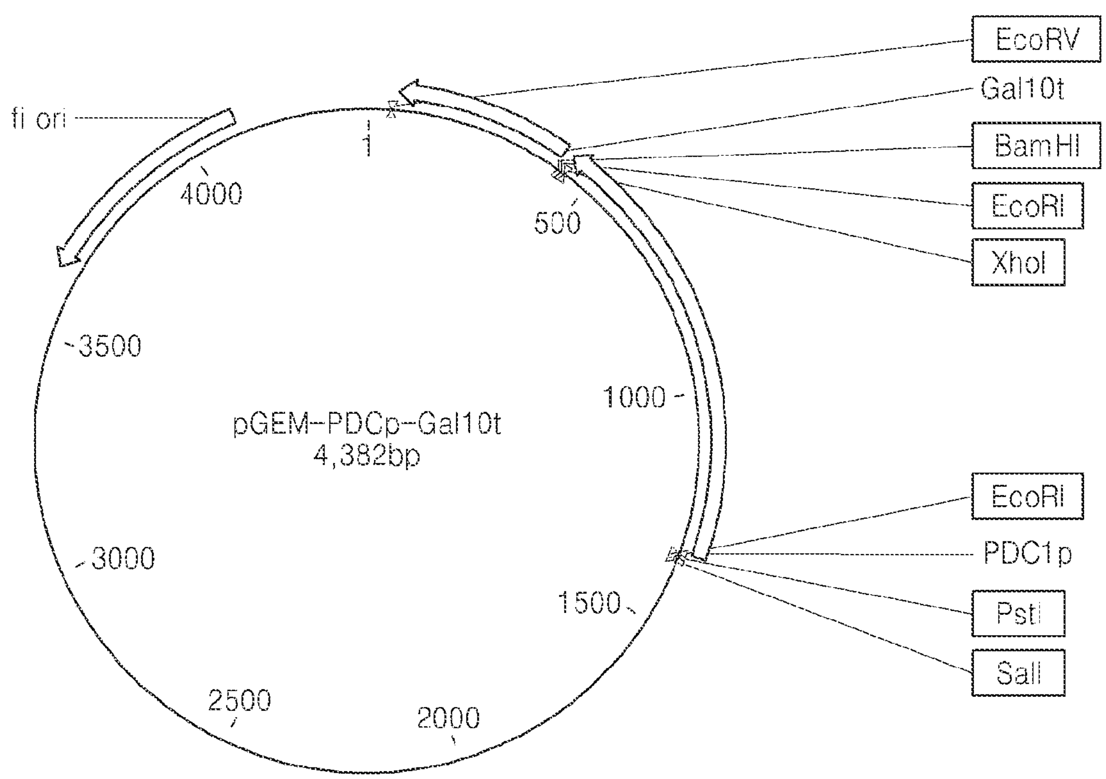
FIG. 1 is a schematic view of a pGEM-PDCp-Gal10t vector.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items.

According to an aspect of the present invention, provided is a yeast cell with an increased activity of a lactate dehydrogenase that converts pyruvate into lactate. In the yeast cell, the lactate dehydrogenase may be derived from a *Sordaria* genus.

According to an aspect of the present invention, a yeast cell includes a gene encoding a lactate dehydrogenase that converts pyruvate into lactate, wherein the lactate dehydrogenase is derived from *Sordaria* genus.

As used herein, the term "lactate" denotes "lactic acid" or a salt thereof.

The terms "sequence identity" refers to the extent that sequences are identical or similar on an amino acid to amino acid basis, or nucleotide to nucleotide basis, over a window of comparison. Thus, a "percentage of sequence identity", for example, can be calculated by comparing two optimally aligned sequences over the window of comparison, determining the number of positions at which the identical amino acid occurs in both sequences to yield the number of matched positions, dividing the number of matched positions by the total number of positions in the window of comparison (i.e., the window size), and multiplying the result by 100 to yield the percentage of sequence identity.

The yeast cell may belong to Ascomycota phylum. The Ascomycota phylum may include Saccharomycotina or Taphrinomycotina subphylum. The yeast cell may belong to Saccharomycetes or Schizosaccharomycetes class. The yeast cell may belong to Saccharomycetaceae family. The saccharomycetaceae may include *Saccharomyces* genus, *Kluyveromyces* genus, *Candida* genus, *Pichia* genus, *Issatchenkia* genus, *Debaryomyces* genus, *Zygosaccharomyces* genus, or *Saccharomycopsis* genus. An example of the *Saccharomyces* genus may be *S. cerevisiae, S. bayanus, S. boulardii, S. bulderi, S. cariocanus, S. cariocus, S. chevalieri, S. dairenensis, S. ellipsoideus, S. eubayanus, S. exiguus, S. florentinus, S. kluyveri, S. martiniae, S. monacensis, S. norbensis, S. paradoxus, S. pastorianus, S. spencerorum, S. turicensis, S. unisporus, S. uvarum*, or *S. zonatus*. The *Kluyveromyces* genus may be *Kluyveromyces thermotolerans*. The *Candida* genus may be *Candida glabrata*. The *Zygosaccharomyces* genus may be *Zygosaccharomyces bailli* or *Zygosaccharomyces rouxii*.

Also, the yeast cell may be a mutant yeast cell for lactate production, or a natural (e.g., wild-type) yeast cell. The mutant yeast cell may be resistant against uracil, sulfuaguanidine, sulfathiazole, azaserine, trimethoprim, or monofluoroacetate.

The yeast cell may have a lactate-producing ability. An activity of a lactate dehydrogenase (Ldh) converting pyruvate into lactate may be increased to a degree sufficient to produce lactate. The activity may be increased about 5% or more, about 10% or more, about 15% or more, about 20% or more, about 30% or more, about 50% or more, about 60% or more, about 70% or more, or about 100% or more compared to an activity of a control group such as a parent yeast cell.

The term "parent cell" denotes a cell not having a specific genetic modification resulting in a genetically engineered cell. The term "wild-type" enzyme, polypeptide or polynucleotide denotes an enzyme, a polypeptide or a polynucleotide not having a specific genetic modification resulting in a genetically engineered enzyme, polypeptide or polynucleotide.

In the yeast cell, the activity of converting pyruvate into lactate may be increased by an increased expression of exogenous lactate dehydrogenase (LDH) enzyme.

The increase of the expression may be caused by introduction of a gene encoding the exogenous lactate dehydrogenase enzyme. The gene may be an exogenous gene. The exogenous gene may be heterologous. An exogenous gene encoding lactate dehydrogenase may be introduced into a downstream position of a promoter that enables expression of a gene encoding lactate dehydrogenase. Also, a polynucleotide encoding lactate dehydrogenase may be integrated in a genome of yeast cell. When a polynucleotide encoding lactate dehydrogenase functions for production of active proteins in a cell, the polynucleotide is considered "functional" in a cell. A polynucleotide encoding lactate dehydrogenase is specific in production of L-Ldh or D-Ldh, and thus a yeast cell including the polynucleotide encoding lactate dehydrogenase may produce an L-lactate enantiomer, a D-lactate enantiomer, or a salt thereof.

The number of copies of the gene encoding the exogenous lactate dehydrogenase may be increased by an introduced gene encoding the lactate dehydrogenase. Also, the number of copies of the gene encoding the exogenous lactate dehydrogenase may be increased by the repetitive introduction of gene encoding the lactated dehydrogenase into different loci of genome.

The yeast cell may include a gene that encodes one lactate dehydrogenase or multiple genes that encodes 1 to 10 copies of lactate dehydrogenase. The multiple genes may encode, for example, 1 to 8, 1 to 5, 1 to 4, or 1 to 3 copies of lactate dehydrogenase. When the yeast cell includes the genes encoding multiple copies of lactate dehydrogenase, each of the genes may be a copy of the same gene or may include a copy of a gene that encodes at least two different lactate dehydrogenases. Multiple copies of a gene encoding exogenous lactate dehydrogenase may be included in the same locus or in multiple loci within a host cell's genome. The exogenous lactate dehydrogenase may have an increased activity compared to an endogenous lactate dehydrogenase of a yeast cell.

The gene encoding the exogenous lactate dehydrogenase may be derived from bacteria, yeast, fungi, mammals, or reptiles. The fungi may belong to *Sordaria* genus. The *Sordaria* genus may be *Sordaria macrospora, Sordaria fimicola, Sordaria alcina, Sordaria araneosa, Sordaria brevicollis, Sordaria equina, Sordaria heterothallis, Sordaria humana, Sordaria lappae, Sordaria sclerogenia, Sordaria superba*, or *Sordaria tomento-alba.*

Also, the increase of expression may be caused by modification of a control region of a gene encoding the exogenous lactate dehydrogenase. Also, the increased in activity of converting pyruvate into lactate may be caused by mutation of the exogenous lactate dehydrogenase.

Moreover, the yeast cell may further include a polynucleotide encoding the exogenous lactate dehydrogenase. The yeast cell may include a vector including the exogenous lactate dehydrogenase derived from bacteria, yeast, fungi, mammals, or reptiles. The vector may include a replication origin, a promoter, a polynucleotide encoding a lactate dehydrogenase, and a terminator. The replication origin may include a yeast autonomous replication sequence (ARS). The yeast ARS may be stabilized by a yeast centrometric sequence (CEN). The promoter may be selected from the group consisting of a CYC promoter, a TEF promoter, a GPD promoter, an ADH promoter, and a CCW12 promoter. The CYC promoter, TEF promoter, CCW12 promoter, and ADH promoter may be, each respectively, have nucleotide sequences of SEQ ID NO: 9, 10, 11, and 12. The terminator may be selected from the group consisting of phosphoglycerate kinase 1 (PGK1), cytochrome c transcription (CYC1), and GAL1. The CYC1 terminator may have a nucleotide sequence of SEQ ID NO: 13. The vector may further include a selection marker.

As used herein, the term "lactate dehydrogenase (Ldh)" may refer to an enzyme that catalyzes conversion of pyruvate to lactate. The lactate dehydrogenase may be a NAD(P)-dependent enzyme, producing L-lactate or D-lactate. The lactate dehydrogenase may act on pyruvate. The NAD(P)-dependent enzyme may be an enzyme that is classified into EC 1.1.1.27 that produces L-lactate or EC 1.1.1.28 that produces D-lactate. The lactate dehydrogenase may have about 65%, 70%, 75%, 80%, 85%, 90%, or 95% more sequence identity with an amino acid sequence of SEQ ID NO: 1, and the gene encoding lactate dehydrogenase may have a nucleotide sequence of SEQ ID NO: 2.

In the yeast cell, the activity of converting pyruvate into acetaldehyde may be eliminated or depressed. As used herein, the term "depressed" may indicate that an activity in the modified yeast cell is reduced compared to a yeast cell of the same type that is not genetically modified (e.g., a wild-type yeast cell).

The yeast cell may have a gene encoding a polypeptide converting pyruvate into acetaldehyde is inactivated, depressed, or reduced.

As used herein, the term "inactivation" may refer to generating a gene that is not expressed at all or a gene that expresses a gene product that has no activity. The term "depression" may refer to generating a gene whose expression level is reduced compared to a parent yeast cell, or a gene which encodes a protein with decreased activity compared to a wild-type protein. The activity of the polypeptide converting pyruvate into acetaldehyde may be about 50% or more, about 55% or more, about 60% or more, about 70% or more, about 75% or more, about 80% or more, about 85% or more, about 90% or more, about 95% or more, or about 100% or more depressed compared to an activity of a control group such as a parent yeast cell or wild-type enzyme.

Activity of a cell, polypeptide, or enzyme may be reduced due to deletion or disruption of a gene encoding the polypeptide or enzyme. As used herein, the "deletion" or "disruption" of the gene includes mutation or deletion of the gene or a regulatory region of the gene (e.g., operator, promoter or terminator regions of the gene), or a part thereof, sufficient to disrupt or delete gene function or the expression of a functional gene product. Mutations include substitutions, insertions, and deletions of one or more bases in the gene or its regulator regions. As a result, the gene is not expressed nor has a reduced amount of expression, or the activity of the encoded protein or enzyme is reduced or eliminated. The deletion or disruption of the gene may be accomplished by any suitable genetic engineering technique, such as homologous recombination, mutagenesis, or molecular evolution. When a cell includes a plurality of copies of the same gene or at least two different polypeptide paralogs, at least one gene may be deleted or disrupted.

The deletion or disruption may be generated by transforming the vector including some sequence of the gene or the fragment of nucleotides in a cell, culturing the cell to allow homologous recombination of the sequence and an endogenous gene of the cell to occur, and selecting the cells in which the homologous recombination occurred by using a selection marker. The selection marker may give prototrophy in minimal media, resistance to a cytotoxic agent, or selectable phenotype such as expression of surface protein.

A polypeptide converting pyruvate into acetaldehyde may be an enzyme that is classified as EC 4.1.1.1. The polypeptide converting pyruvate into acetaldehyde may have about 65%, 70%, 75%, 80%, 85%, 90%, or 95% more sequence identity with an amino acid sequence of SEQ ID NO: 3. A gene that encodes the pyruvate into acetaldehyde may have a nucleotide sequence of SEQ ID NO: 4. The gene may be pdc1 or pdc2 that encodes pyruvate decarboxylase (Pdc).

The yeast cell may have increased activity of converting pyruvate into lactate, wherein the yeast cell includes lactate dehydrogenase which is derived from a microorganism of the *Sordaria* genus; a gene encoding the lactate dehydrogenase is introduced therein; and a gene encoding a polypeptide that converts pyruvate into acetaldehyde is inactivated or depressed. The yeast cell may have a Deposit No. KCTC 12443BP. The yeast cell may produce lactate at a yield of about 1.50% to about 1.95% or more, for example, about 1.70% to about 1.95% or more, about 1.75% to about 1.95% or more, about 1.8% to about 1.95% or more, about 1.85% to about 1.95% or more, or about 1.90% to about 1.95% or more, which is a gram/gram ratio of a lactate production to a consumed amount of glucose.

Also, activity of converting lactate into pyruvate, activity of converting dehydroxyacetone phosphate (DHAP) into glycerol-3-phosphate, or a combination thereof in the yeast cell may be removed or depressed.

The yeast cell may include a gene that encodes a polypeptide converting lactate into pyruvate, which is inactivated or depressed in activity. The polypeptide converting lactate into pyruvate may be a cytochrome c-dependent enzyme. The polypeptide converting lactate into pyruvate may be lactate cytochrome-c-oxydoreductase (Cyb2). The lactate cytochrome-c-oxydoreductase may be an enzyme that is classified to EC 1.1.2.4 that acts on D-lactate or EC 1.1.2.3 that acts on L-lactate. The polypeptide converting lactate into pyruvate may have about 65%, 70%, 75%, 80%, 85%, 90%, or 95% more sequence identity with an amino acid sequence of SEQ ID NO: 5. The gene encoding the polypeptide converting lactate into pyruvate may have a nucleotide sequence of SEQ ID NO: 6.

The yeast cell may include a gene encoding polypeptide converting dehydroxyacetone phosphate (DHAP) into glycerol-3-phosphate, which may be inactivated or depressed. The polypeptide converting dehydroxyacetone phosphate (DHAP) into glycerol-3-phosphate may be an enzyme catalyzing reduction of dehydroxyacetone phosphate (DHAP) into glycerol-3-phosphate by using oxidation of NAD(P)H into NAD(P)+. The enzyme may be an enzyme classified into EC 1.1.1.8. The polypeptide may be cytosolic glycerol-3-phosphate dehydrogenase (GPD1). The polypeptide converting dehydroxyacetone phosphate (DHAP) into glycerol-3-phosphate may have about 65%, 70%, 75%, 80%, 85%, 90%, or 95% more sequence identity with an amino acid sequence of SEQ ID NO: 7. The gene encoding the polypeptide converting dehydroxyacetone phosphate (DHAP) into glycerol-3-phosphate may have a nucleotide sequence of SEQ ID NO: 8. The gene may be gpd1 encoding glycerol-3-phosphate dehydrogenase.

In one embodiment, the yeast cell having increased activity of converting pyruvate into lactate, wherein the yeast cell includes lactate dehydrogenase which is derived from a *Sordaria* genus organism; and wherein a gene encoding a polypeptide that converts pyruvate into acetaldehyde, a gene encoding a polypeptide that converts lactate into pyruvate, and a gene encoding a polypeptide that converts dehydroxyacetone phosphate (DHAP) into glycerol-3-phosphate is inactivated or depressed. The yeast cell may produce lactate at a yield of about 57.20% to about 58.50% or more, for example, about 57.50% to about 58.50% or more, about 57.53% to about 58.50% or more, about 57.53% to about 58.45% or more, or about 57.53% to about 58.40% or more, that is a ratio of a lactate production to a consumed amount of glucose.

An expression vector including a polynucleotide that encodes the lactate dehydrogenase is provided for manufacture of a yeast cell in which activity of lactate dehydrogenase converting pyruvate into lactate is increased or an introduced gene encoding lactate dehydrogenase converting pyruvate into lactate is included, and the lactate dehydrogenase is derived from a *Sordaria* genus organism.

The polynucleotide may be operably connected with a regulatory sequence appropriate for expressing a polynucleotide in an appropriate host. The regulatory sequence may include a promoter, a terminator, or an enhancer. Also, the promoter may be operably connected with a sequence encoding a gene. As used herein, the term "operably connected" may refer to a functional connection between a nucleic acid expression regulatory sequence and another nucleotide sequence. In this regard, the regulatory sequence may regulate transcription and/or translation of a nucleotide sequence encoding the gene.

The yeast expression vector may be, for example, a vector for expression in *Saccharomyces cerevisiae*. Examples of the yeast expression vector include pYepSec1, 2i, pAG-1, Yep6, Yep13, PEMBLYe23, pMFa, pJRY88, or pYES2.

In order to act as an expression vector, the yeast expression vector may include a replication origin, a promoter, a multiple cloning site (MCS), and/or a selection marker. The replication origin enables a plasmid to replicate separately from a chromosome of a host cell. The promoter functions in a transcription process of an inserted foreign gene. The MCS enables a foreign gene to be inserted through various restriction enzyme sites. The selection marker serves to confirm whether the vector correctly inserted in the host cell. The selection marker may include an antibiotic resistance gene. Examples of the resistance genes are genes that are resistant to ampicillin, gentamicin, carbenicillin, chloramphenicol, streptomycin, kanamycin, geneticin, neomycin, and tetracycline. Also, the selection marker may include an auxotrophic gene, for example, a gene providing an autotrophic property against one selected from uracil, tryptophan, leucine, and histidine.

According to another embodiment of the present disclosure, a method of producing lactate is provided, wherein the method includes culturing the yeast cell described above, and collecting lactate from the culture.

The culturing of the yeast cell may be performed in a medium containing a carbon source, for example glucose. The medium used in the culturing of the yeast cell may be a common medium appropriate in growth of a host cell which is the same as a minimum or composite medium containing an appropriate replenisher. The appropriate medium may be a commercial product found in the market or may be manufactured according to a known manufacturing method.

The medium used in the culturing of the yeast cell may be a medium satisfying the growing conditions of a particular yeast cell. The medium may be a medium selected from the group consisting of a carbon source, a nitrogen source, a salt, a microelement, and a combination thereof.

The culture condition for obtaining lactate from the mutant yeast cell may be appropriately controlled. The cell is cultured under an aerobic condition for cell proliferation. Then, the cell is cultured under an anaerobic condition for lactate production. The anaerobic condition may include a microaerobic condition having a dissolved oxygen (DO) concentration in a range of 0% to 10%, for example, 0% to 8%, 0% to 6%, 0% to 4%, or 0% to 2%. A pH of a fermented solution may be controlled to be maintained in a range of about 2 to about 7.

The culturing of the yeast cell may be a continuous type, a semi-continuous type, a batch type, or a combination thereof.

The term "culture condition" indicates a condition for culturing a yeast cell. Such culture condition may be, for example, a carbon source, a nitrogen source, or an oxygen condition for the yeast cell to use. The carbon source used by the yeast cell includes monosaccharides, disaccharides, or polysaccharides. In particular, the carbon source may be glucose, fructose, mannose, or galactose. The nitrogen source used by the yeast cell may include an organic nitrogen compound or an inorganic nitrogen compound. In particular, the nitrogen source may be an amino acid, amide, amine, a nitrate, or an ammonium salt. The oxygen condition for culturing the yeast cell includes an aerobic condition of a normal oxygen partial pressure, a low-oxygen condition including 0.1% to 10% of oxygen in the atmosphere, or an anaerobic condition without oxygen. A metabolic pathway may be modified in accordance with the carbon source or the nitrogen source that may be practically used by the yeast cell.

The obtaining of the lactate from the culture may be performed by separating the lactate from the culture by using a method commonly known in the art. The separation method may be centrifuge, filtration, ion-exchange chromatography, or crystallization. For example, the culture may be centrifuged at a low rate to remove a biomass, and the supernatant resulting therefrom may be separated through ion-exchange chromatography.

The present disclosure will be described in further detail with reference to the following examples. These examples are for illustrative purposes only and are not intended to limit the scope of the present disclosure.

Example 1

Preparation of Lactate Dehydrogenase (L-Ldh) Overexpression Vector for Lactate Production A cassette for overexpressing lactate dehydrogenase (L-Ldh) was manufactured in the manner as follows. Polymerase Chain Reaction (PCR) (at a temperature of 95° C. for 4 minutes, 30 times repeated at a temperature of 94° C. for 30 seconds, at a temperature of 52° C. for 30 seconds, at a temperature of 72° C. for 1 minute, and then at a temperature of 72° C. for 10 minutes) was performed by using genomic DNA of *Saccharomyces cerevisiae* (CEN.PK2-1D, genotype: MATα ura3-52; trp1-289; leu2-3,112; his3 Δ 1; MAL2-8$^{C}$; SUC2, EUROSCARF accession number: 30000B) as a template and primers of SEQ ID NOS: 14 and 15 to clone a promoter part (CCW12p) of CCW12 gene known for inducing gene expression in *Saccharomyces cerevisiae*, cleaving the PCR fragment resulting therefrom with SacI and XbaI, and introducing the cleaved resultant into p416-GPD (ATCC® 87360™) to prepare p416-CCW12p.

Then, L-Ldh gene (SmLDH) (available from Cosmogenetch) of SEQ ID NO: 2 derived from *Sordaria macrospora* was cleaved with a restriction enzyme EcoRI and HindIII, and the cleaved resultant was ligated to p416-CCW12p to prepare p416-CCW12-SmLDH.

Example 2

Preparation of pdc1 Gene Deletion Cassette

A gene deletion vector was prepared in the manner as follows to delete pyruvate decarboxylase 1 (PDC1) gene involved in production of ethanol from pyruvate by using a homologous recombination method.

To use an antibiotic marker, a Gal10 terminator (Gal10t) PCR fragment was prepared by using a genome DNA of *Saccharomyces cerevisiae* (*S. cerevisiae*, CEN.PK2-1D) as a template and primers of SEQ ID NOS: 16 and 17, cleaving the Gal10t PCR fragment with NotI, and introducing the cleaved resultant to pGEM-5Zf (Promega USA) to prepare pGEM-Gal10t.

Also, a PDC promoter (PDCp) was the result of performing PCR with a genome DNA of *Saccharomyces cerevisiae* (*S. cerevisiae*, CEN.PK2-1D) by using SEQ ID NOS: 18 and 19, cleaving the fragment resulting therefrom with EcoRI, and ligating the cleaved resultant to pGEM-Gal10t cleaved with the same EcoRI to prepare pGEM-PDCp-Gal10t. FIG. 1 is a schematic view of a pGEM-PDCp-Gal10t vector. The pGEM-PDCp-Gal10t vector was further prepared to overexpress in the yeast cell by inserting NPT, which is a geneticin antibiotic resistance gene.

Figure 2:
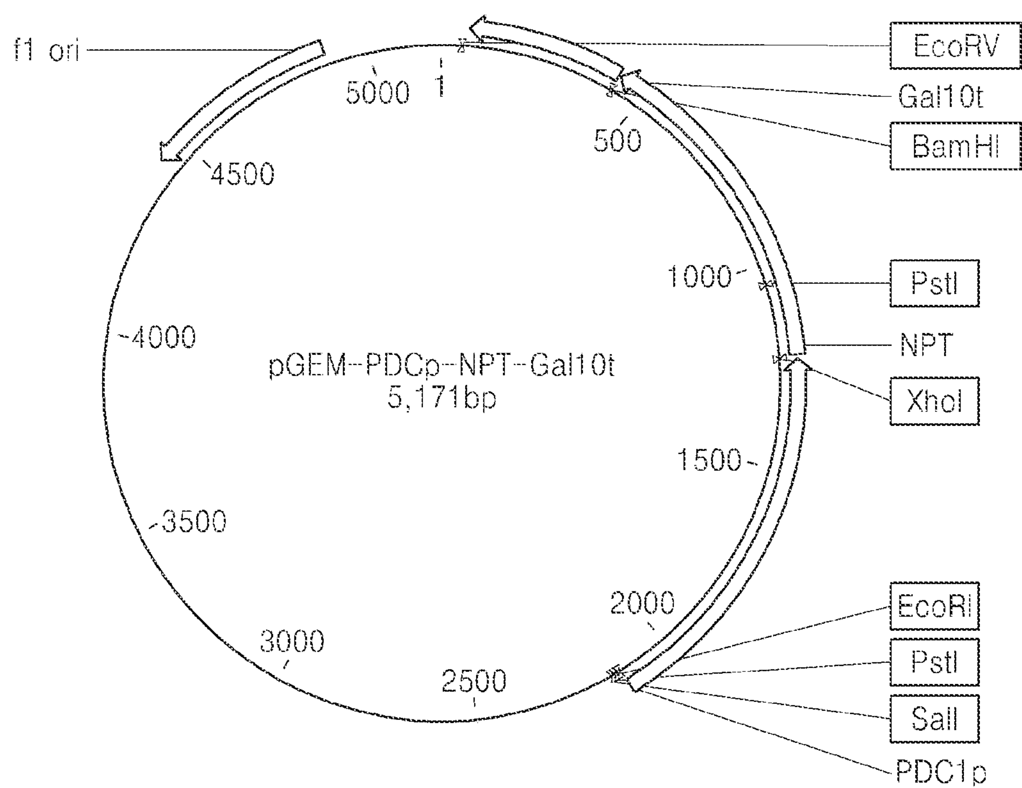
FIG. 2 is a schematic view of a pGEM-PDCp-NPT-Gal10t vector.

Then, a neomycin phosphotransferase (NPT) gene capable of giving tolerance to geneticin (G418) antibiotics was cloned by performing PCR using primers of SEQ ID NOS: 20 and 21 and pcDNA3.3-TOPO (available from Invitrogen) as a template. The fragment thus resulting was cleaved with XhoI and BamHI, and the resultant was ligated to pGEM-PDCp-Gal10t, which is cleaved with the same restriction enzymes, to prepare pGEM-PDCp-NPT-Gal10t. FIG. 2 is a schematic view of a pGEM-PDCp-NPT-Gal10t vector. The pGEM-PDCp-NPT-Gal10t vector is an NPT overexpression deletion vector, which becomes a template in preparation of a cassette for deleting PDC1.

A pdc1 gene deletion cassette was prepared by performing PCR by using pGEM-PDCp-NPT-Gal10t as a template and primers of SEQ ID NOS: 22 and 23.

Example 3

Preparation of *Saccharomyces cerevisiae* Strain from which PDC1 is Deleted

Figure 3:
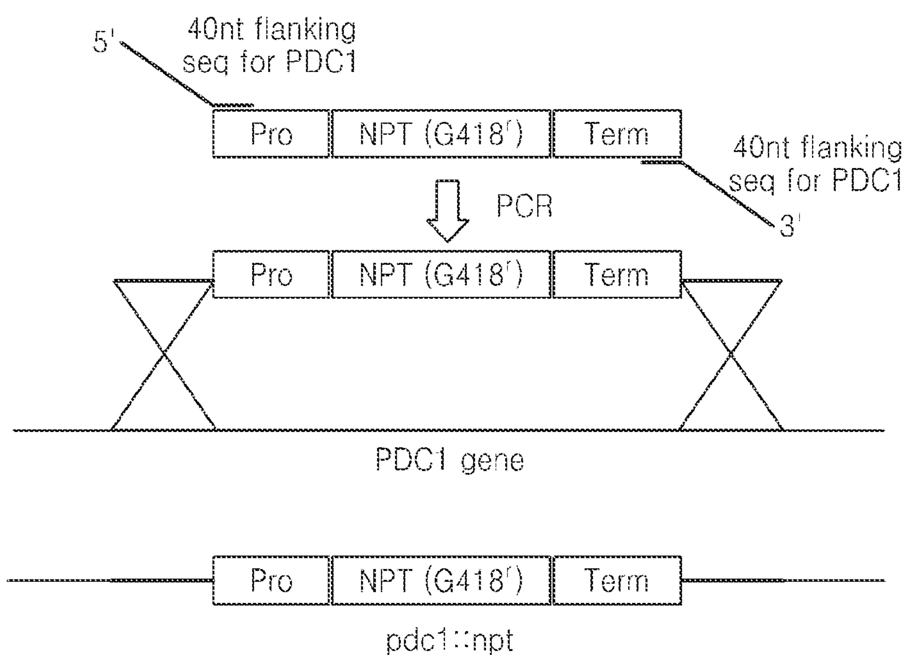
FIG. 3 is a schematic drawing depicting a process of preparing a mutant strain by deleting PDC1 from a mother strain, *Saccharomyces cerevisiae* CEN.PK2-1D.

A mutant strain, which is PDC1-deficient *Saccharomyces cerevisiae*, was prepared in the manner as follows. FIG. 3 illustrates a process of preparing the mutant strain, which is prepared by deleting PDC1 from a mother strain, *Saccharomyces cerevisiae* CEN.PK2-1D. *Saccharomyces cerevisiae* CEN.PK2-1D was smeared on a YPD (10 g of a yeast extract, 20 g of peptone, 20 g of glucose) solid medium and cultured for about 24 hours at a temperature of about 30° C., and then a colony resulting from there was inoculated in about 10 ml of a YPD liquid medium for about 18 hours at a temperature of about 30° C. The sufficiently grown medium was inoculated in about 50 ml of a YPD liquid medium at a concentration of 1% (v/v) contained in a 250 ml-flask, and cultured in an incubator at a rate of about 230 rpm and a temperature of about 30° C. After about 4 to 5 hours, when optical density at 600 nm ($OD_{600}$) was about 0.5, the culture was centrifuged at a rate of about 4,500 rpm for about 10 minutes to obtain *Saccharomyces cerevisiae* cells, and the cells were resuspended in a lithium acetate solution at a concentration of about 100 mM. Then, the cells were centrifuged at a rate of about 4,500 rpm for about 10 minutes to obtain resuspended cells, resuspended in a lithium acetate solution at a concentration of about 1 M added with 15% of glycerol, and then divided into a volume of about 100 ul each.

In order to delete PDC1, the PDC1 gene deletion cassette prepared in Example 2 was mixed with mixed with 50% of polyethylene glycol and a single stranded carrier DNA and reacted in a water tub at a temperature of about 42° C. for about 1 hour, and then, the culture solution was smeared on a YPD medium containing about 100 ug/ml of geneticin in a plate and cultured at a temperature of about 30° C. for about 24 hours or more. 8 colonies (a mutant strain) formed in the plate were selected, transferred to another YPD solid medium, and, at the same time, cultured in a liquid medium including the same components contained in the YPD solid medium to separate genome DNA from the strain by using a commonly used kit (Gentra Puregene Cell kit, Qiagen, USA). In order to confirm deletion of PDC1 by performing PCR having the separated genome DNA of the modified strain as a template and using primers of SEQ ID NOS: 24 and 25, and then, electrophoresis was performed on the resulting PCR product to confirm the PDC1 deletion. As a result, *Saccharomyces cerevisiae* CEN.PK2-1D (pdc1::NPT) was obtained.

Example 4

Introduction of L-LDH Overexpression Vector Derived from *Sordaria macrospora* to PDC1-Deleted *Saccharomyces cerevisiae*

(4.1) Preparation of Strain to which L-LDH Overexpression Vector Derived from *Sordaria macrospora* to PDC1-Deleted *Saccharomyces cerevisiae* is Introduced The p416-CCW12-SmLDH plasmid prepared in Example 1 was inserted into a PDC1-deleted *Saccharomyces cerevisiae* CEN.PK2-1D (pdc1::NPT) strain in Example 3 as follows.

The p416-CCW12-SmLDH plasmid prepared in Example 1 was mixed with 50% of polyethyleneglycol and a single stranded carrier DNA and reacted in a water tub at a temperature of about 42° C. for about 1 hour, and then, the culture solution was smeared on a uracil-free minimal medium (including YSD, 6.7 g/L of yeast nitrogen base without amino acids, and 1.4 g/L of amino acid dropout mix (−ura)) in a plate and cultured at a temperature of about 30° C. for about 24 hours or more.

8 colonies (a mutant strain) formed in the plate were selected, transferred to another uracil-free minimal medium, and at the same time, cultured in a liquid medium including the same components contained in the uracil-free minimal medium to separate plasmid DNA from the strain by using a commonly used kit (Yeast plasmid isolation kit, Clontech). In order to confirm a plasmid including SmLDH, PCR was performed by using the separated plasmid DNA as a template and primers of SEQ ID NOS: 26 and 27, and then, electrophoresis was performed on the resulting PCR product to confirm that the inserted plasmid was p416-CCW12-SmLDH. As a result, *Saccharomyces cerevisiae* CEN.PK2-1D (pdc1::NPT+SmLDH) was obtained.

*Saccharomyces cerevisiae* CEN.PK2-1D (pdc1::NPT+SmLDH), which was prepared by introducing an L-LDH overexpression vector derived from *Sordaria macrospora* into the PDC1-deleted *Saccharomyces cerevisiae*, was deposited in Korean Collection for Type Cultures (KCTC) on Jul. 11, 2013, and received an Deposit number, KCTC 12443 BP.

(4.2) Preparation of Strain by Introducing L-LDH Overexpression Vector Derived from *Pelodiscus sinensis japonicus* into PDC1-Deleted *Saccharomyces cerevisiae*

PCR was performed by using genome DNA of L-LDH (PsLDH) (SEQ ID NO: 28) derived from *Pelodiscus sinensis japonicus* as a template and primers of SEQ ID NOS: 29 and 30. Then, the PCR fragment resulting therefrom and p416-CCW12p prepared in Example 1 were cleaved with BamHI and SalI, and the cleaved resultant was ligated to prepare an L-ldh expression vector, p416-CCW12p-LDH.

Figure 4:
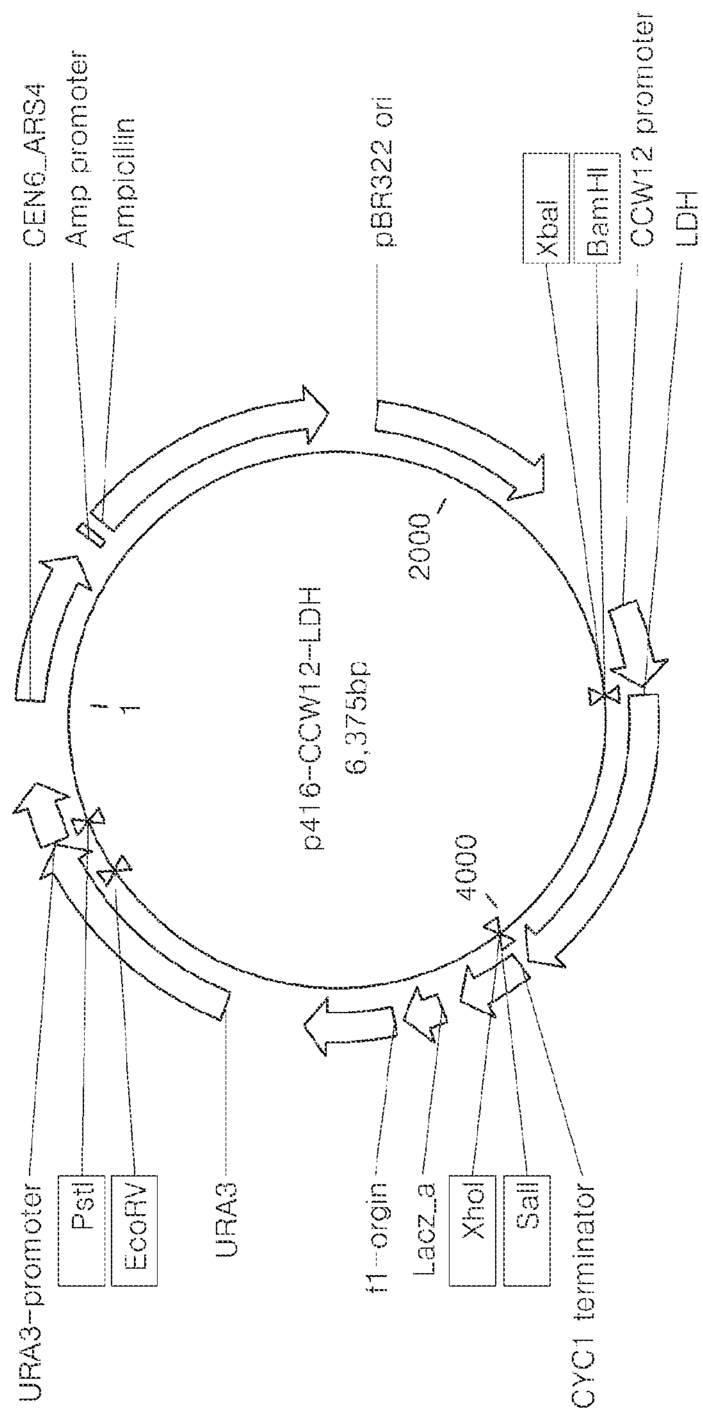
FIG. 4 is a schematic view of a p416-CCW12p-LDH vector.

Also, the L-LDH expression vector had a yeast autonomous replication sequence/a yeast centrometric sequence of SEQ ID NO: 30, a CYC promoter of SEQ ID NO: 9, a CCW12 promoter of SEQ ID NO: 11, and a CYC1 terminator of SEQ ID NO: 13, wherein the L-LDH expression vector included a polynucleotide encoding L-LDH derived from *Pelodiscus sinensis japonicus* of SEQ ID NO: 28. FIG. 4 illustrates a p416-CCW12p-LDH vector. As shown in FIG. 4, LDH gene derived from *Pelodiscus sinensis japonicus* (PsLDH gene) was introduced to the vector.

The prepared p416-CCW12p-LDH vector was mixed with 50% of polyethyleneglycol and a single stranded carrier DNA and reacted in a water tub at a temperature of about 42° C. for about 1 hour, and then, the culture solution was smeared on a uracil-free minimal medium (including YSD, 6.7 g/L of yeast nitrogen base without amino acids, and 1.4 g/L of amino acid dropout mix (−ura)) in a plate and cultured at a temperature of about 30° C. for about 24 hours or more.

8 colonies (a mutant strain) formed in the plate were selected, transferred to another YSD (−ura) solid medium, and at the same time, cultured in a YSD (−ura) liquid medium to separate plasmid DNA from the strain by using a commonly used kit (Yeast plasmid isolation kit, Clontech). In order to confirm a plasmid including PsLDH, PCR was performed by using the separated plasmid DNA as a template and primers of SEQ ID NOS: 29 and 30, and then, electrophoresis was performed on the resulting PCR product to confirm that the inserted plasmid was p416-CCW12-PsLDH. As a result, *Saccharomyces cerevisiae* CEN.PK2-1D (pdc1::NPT+PsLDH) was obtained.

Example 5

Production of L-Lactate by Using a *Saccharomyces cerevisiae* Strain, to which L-Ldh Derived from *Sordaria macrospora* is Introduced

*Saccharomyces cerevisiae CEN.PK*2-1 D (pdc1::NPT+SmLDH) prepared in Example 1 was smeared on a YSD (−ura) solid medium and cultured for about 24 hours at a temperature of about 30° C., and then the culture was inoculated in 50 ml of a YSD (−ura) medium including 40 g/L of glucose and cultured for about 16 hours at a temperature of about 30° C.

Then fermentation was performed by quantifying an amount by measuring about 5.0 of cells concentration in 50 ml of the *Saccharomyces cerevisiae CEN.PK*2-1D (pdc1::NPT+SmLDH) culture solution by using a spectrophotometer at about 600 nm of an optical density (OD), centrifuging to remove the supernatant, resuspending the cells, and re-inoculating into about 50 ml of a new YSD (−ura) including about 40 g/L of glucose. The cells were fermented by culturing the cells in a stirring incubator maintaining a rate at about 90 rpm at a temperature of about 30° C. for about 8 hours. During the fermentation, samples were periodically resulting from the flask, centrifuged at a rate of 13,000 rpm for about 10 minutes, and then the supernatant resulting from each of the samples was analyzed for concentrations of various metabolic products, lactate, and glycerol by using a high-pressure liquid chromatography (HPLC).

In addition, *Saccharomyces cerevisiae* CEN.PK2-1D (pdc1::NPT+PsLDH) prepared in Example 4.2 was also cultured and fermented in the same manner described above, and then concentrations of various metabolic products, lactate, and glycerol of the samples were analyzed by using a high-pressure liquid chromatography (HPLC).

As shown in Table 1, the SmLDH overexpression vector-introduced strain had a better lactate productivity and an increased percent yield as well compared to the L-Ldh (PsLDH) derived from *Pelodiscus sinensis japonicus*-introduced strain. The lactate productivity and the percent yield of the SmLDH overexpression vector-introduced strain were respectively increased from about 610 mg/L to about 1,110 mg/L and from about 1.69% to about 1.94% compared to the PsLDH overexpression vector, which was the control group.

TABLE 1

| Vector introduced into PDC1-deleted *Saccharomyces cerevisiae* | % yield (g/g) | Lactate (mg/L) | Glycerol (g/L) |
|---|---|---|---|
| SmLDH overexpression vector | 1.94 | 1,110 | 1.34 |
| PsLDH overexpression vector | 1.69 | 610 | 1.07 |
| Control | 0.00 | 0.00 | 1.11 |

SmLDH: L-LDH derived from *Sordaria macrospora*
PsLDH: L-LDH derived from *Pelodiscus sinensis japonicus*
control: an empty vector

Example 6

Preparation of Strain and Expression Vector for Highly Efficient Production of Lactate

*Saccharomyces cerevisiae* (*S. cerevisiae* CEN.PK2-1D (MATα ura3-52; trp1-289; leu2-3,112; his3 Δ 1; MAL2-8C; SUC2)) was used as a lactate production strain. Then, a main enzyme of alcohol fermentation, a pyruvate decarboxylase (PDC1) gene, a main enzyme of glycerol biosynthesis, a NAD-dependent glycerol-3-phosphate dehydrogenase (GPD1) gene, and a lactate breakdown enzyme, an L-lactate cytochrome-c oxidoreductase2 (CYB2) gene were removed to block production pathways of ethanol and glycerol, which are main by-products of lactate production. Also, at the same time removing the three genes, a lactate dehydrogenase (LDH) gene of SEQ ID NO: 28 was simultaneously inserted to a location from which each of the genes was removed, and thus 3 copies of lactate dehydrogenase were inserted for lactate production.

The removal of each of the genes and the simultaneous insertion of the LDH gene were performed by homologous recombination at an upper stream part and a lower stream part of an open reading frame or a target locus of a region including a promoter and a terminator of each of the genes.

(6.1) Preparation of L-LDH Overexpression Vector and PDC1, GPD1, and CYB2 Gene-Inactivation Vector

(6.1.1) Preparation of L-LDH Overexpression Vector

For overexpression of L-LDH, PCR was performed by using genome DNA of *Saccharomyces cerevisiae* CEN.PK2-1D as a template and primers of SEQ ID NOS: 32 and 33, the CCW12 promoter PCR fragment thus resulting was cleaved with SacI and XbaI, and the cleaved resultant was introduced to p416-GPD (ATCC® 87360™), from which a GPD promoter was cleaved with SacI and XbaI to prepare p416-CCW12p. Then, PCR was performed by using genome DNA of L-LDH (PsLDH) (SEQ ID NO: 28) derived from *Pelodiscus sinensis japonicus* as a template and primers of SEQ ID NOS: 29 and 30, the resulting PCR fragment thus and the prepared p416-CCW12p were cleaved with BamHI and SalI, and the cleaved resultants were ligated to prepare an L-LDH expression vector, p416-CCW12p-PsLDH.

In addition, the L-LDH expression vector included a yeast autonomous replication sequence/a yeast centrometric sequence of SEQ ID NO: 31, a CYC promoter of SEQ ID NO: 9, a CCW12 promoter of SEQ ID NO: 11, and a CYC1 terminator of SEQ ID NO: 13, wherein the L-LDH expression vector included a polynucleotide encoding L-LDH derived from *Pelodiscus sinensis japonicus*.

(6.1.2) Preparation of Gene Exchange Vector

Figure 5:
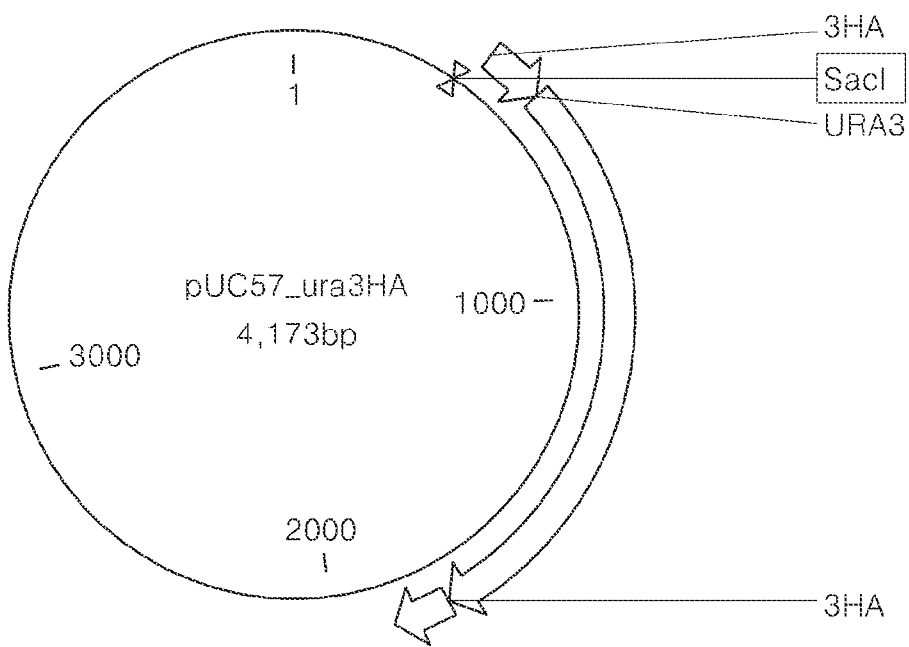
FIG. 5 is a schematic view of a pUC57-ura3HA (Genetics 116: 541-545, August, 1987) vector.
Figure 6:
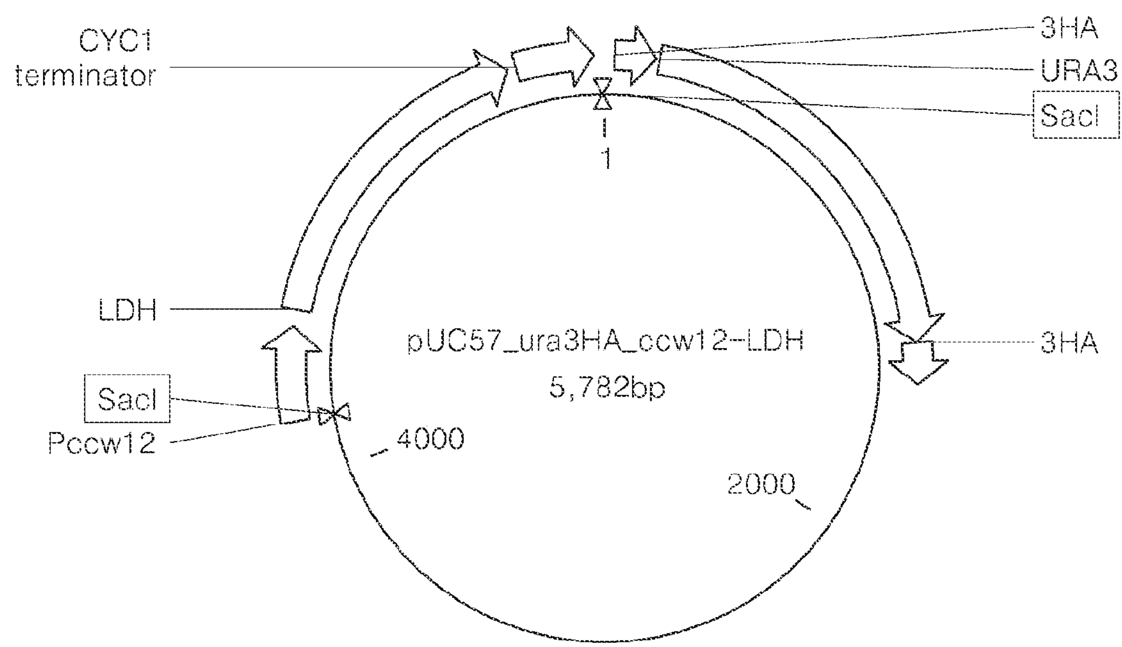
FIG. 6 is a schematic view of a pUC57-ura3HA-CCW12p-LDH vector.
Figure 7:
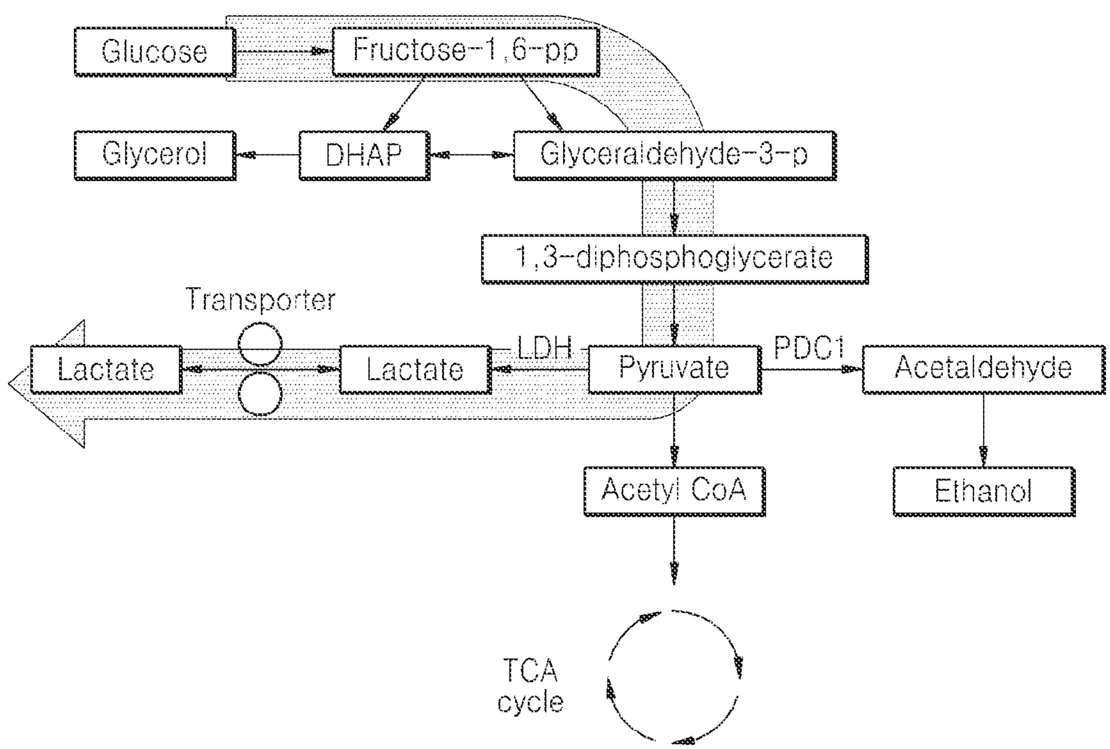
FIG. 7 is a schematic view of a pathway from producing lactate in a yeast cell.

A gene exchange vector was manufactured in the manner as follows to insert an L-LDH gene at the same time deleting PDC1, CYB2, and GPD1 genes by homologous recombination. FIG. 5 illustrates a pUC57-ura3HA (Genetics 116: 541-545, August, 1987) vector. FIG. 6 illustrates a pUC57-ura3HA-CCW12p-LDH vector.

PCR was performed by using the prepared p416-CCW12p-LDH as a template and primers of SEQ ID NOS: 34 and 35, the resulting PCR fragment and the prepared pUC57-ura3HA vector were cleaved with SacI, and then the cleaved resultants were ligated to prepare pUC57-ura3HA-CCW12p-LDH.

In order to prepare a PDC1 gene deletion cassette, PCR was performed by using the prepared pUC57-ura3HA-CCW12p-LDH as a template and primers of SEQ ID NOS: 36 and 37.

In order to prepare a CYB2 gene deletion cassette, PCR was performed by using the prepared pUC57-ura3HA-CCW12p-LDH as a template and primers of SEQ ID NOS: 38 and 39.

In order to prepare a GPD1 gene deletion cassette, 2 cycles of PCR was performed by using the prepared pUC57-ura3HA-CCW12p-LDH as a template and primers of SEQ ID NOS: 40 and 41.

(6.2) Inactivating PDC1, GPD1, and CYB2 Genes

A mutant strain, which is PDC1-deleted *Saccharomyces cerevisiae* CEN.PK2-1D was manufactured in the manner as follows. *Saccharomyces cerevisiae* CEN.PK2-1D was smeared on a YPD solid medium (10 g of a yeast extract, 20 g of peptone, 20 g of glucose) and cultured for about 24 hours at a temperature of about 30° C., and then a colony resulting from there was inoculated in about 10 ml of a YPD liquid medium for about 18 hours at a temperature of about 30° C. The sufficiently grown medium was inoculated in about 50 ml of a YPD liquid medium at a concentration of 1% (v/v) contained in a 250 ml-flask, and cultured in an incubator at a rate of about 230 rpm and a temperature of about 30° C. After about 4 to 5 hours, when $OD_{600}$ was about 0.5, the culture was centrifuged at a rate of about 4,500 rpm for about 10 minutes to obtain *Saccharomyces cerevisiae* cells, and the cells were resuspended in a lithium acetate solution at a concentration of about 100 mM. Then, the cells were centrifuged at a rate of about 4,500 rpm for about 10 minutes to obtain resuspended cells, resuspended in a lithium acetate solution at a concentration of about 1 M added with 15% of glycerol, and then divided into a volume of about 100 ul each.

In order to delete PDC1 gene, the PDC1 deletion cassette prepared in Example 6.1.2 was mixed with 50% of polyethyleneglycol and a single stranded carrier DNA and reacted in a water tub at a temperature of about 42° C. for about 1 hour, and then, the culture solution was smeared on a uracil-free minimal medium (including YSD, 6.7 g/L of yeast nitrogen base without amino acids, and 1.4 g/L of amino acid dropout mix (−ura)) in a plate and cultured at a temperature of about 30° C. for about 24 hours or more. 10 colonies (a mutant strain) formed in the plate were selected, transferred to another YSD (−ura) minimal solid medium, and at the same time, cultured in a YSD (−ura) liquid medium to separate genome DNA from the strain by using a commonly used kit (Gentra Puregene Cell kit, Qiagen, USA). In order to confirm pdc1 deletion, PCR was performed by using the separated genome DNA of the mutant strain as a template and primers of SEQ ID NOS: 42 and 43, and then, electrophoresis was performed on the resulting PCR product. As a result, *Saccharomyces cerevisiae* CEN.PK2-1D (pdc1::PsLDH+URA3) was obtained. Also, URA3 gene, as a selection marker of the PDC1 deletion cassette introduced for preparation of the CEN.PK2-1D (pdc1::PsLDH+URA3) strain, was removed in the manner as follows for additional gene deletion by using the gene deletion vector. *Saccharomyces cerevisiae* CEN.PK2-1D (pdc1::PsLDH+URA3) was inoculated in about 10 ml of a YPD liquid medium and cultured for about 18 hours at a temperature of about 30° C., and then, the culture solution a 5-FOA (including YSD, 6.7 g/L of a yeast nitrogen base without amino acids, 1.4 g/L of an amino acid dropout mix, and 1 μg/L of 5-fluoroorotic acid) solid medium and cultured in a plate at a temperature of about 30° C. for about 24 hours or more. 10 colonies (a URA3 pop-out strain) formed in the plate were selected, transferred to another 5-FOA solid medium, and at the same time, cultured in a YSD liquid medium to separate genome DNA from the strain by using a commonly used kit (Gentra Puregene Cell kit, Qiagen, USA). In order to confirm URA3 pop-out, PCR was performed by using the separated genome DNA of the URA3 pop-out strain as a template and primers of SEQ ID NOS: 42 and 43, and then, electrophoresis was performed on the resulting PCR product. As a result, *Saccharomyces cerevisiae* CEN.PK2-1D (pdc1::PsLDH) was obtained.

A mutant strain, CYB2 deleted *Saccharomyces cerevisiae* CEN.PK2-1D (pdc1::PsLDH), was prepared in the same manner as follows. The resulting *Saccharomyces cerevisiae* CEN.PK2-1D (pdc1::PsLDH) was smeared was smeared on a YPD solid medium (10 g of a yeast extract, 20 g of peptone, 20 g of glucose) and cultured for about 24 hours at a temperature of about 30° C., and then a colony resulting from there was inoculated in about 10 ml of a YPD liquid medium for about 18 hours at a temperature of about 30° C. The sufficiently grown medium was inoculated in about 50 ml of a YPD liquid medium at a concentration of 1% (v/v) contained in a 250 ml-flask, and cultured in an incubator at a rate of about 230 rpm and a temperature of about 30° C. After about 4 to 5 hours, when $OD_{600}$ was about 0.5, the culture was centrifuged at a rate of about 4,500 rpm for about 10 minutes to obtain *Saccharomyces cerevisiae* cells, and the cells were resuspended in a lithium acetate solution at a concentration of about 100 mM. Then, the cells were centrifuged at a rate of about 4,500 rpm for about 10 minutes to obtain cells, resuspended in a lithium acetate solution at a concentration of about 1 M added with 15% of glycerol, and then divided into a volume of about 100 ul each.

In the same manner used in the PDC1 gene deletion, to remove CYB2 gene, the CYB2 deletion cassettes prepared in Examples 6.1 were mixed with 50% of polyethyleneglycol and a single stranded carrier DNA and reacted in a water tub at a temperature of about 42° C. for about 1 hour, and then, the culture solution was smeared on a uracil-free minimal medium (including YSD, 6.7 g/L of yeast nitrogen base without amino acids, and 1.4 g/L of amino acid dropout mix (−ura)) in a plate and cultured at a temperature of about 30° C. for about 24 hours or more. 10 colonies (a mutant strain) formed in the plate were selected, transferred to another YSD (−ura) minimal solid medium, and at the same time, cultured in a YSD (−ura) liquid medium to separate genome DNA from the strain by using a commonly used kit (Gentra Puregene Cell kit, Qiagen, USA). In order to confirm cyb2 deletion, PCR was performed by using the separated genome DNA of the mutant strain as a template and primers of SEQ ID NOS: 44 and 45, and then, electrophoresis was performed on the resulting PCR product. As a result, *Saccharomyces cerevisiae* CEN.PK2-1D (pdc1::PsLDH cyb2::PsLDH+URA3) was obtained.

Also, for additional gene deletion by using the gene deletion vector, URA3 gene, as a selection marker of the PDC1 deletion cassette introduced for preparation of the CEN.PK2-1D (pdc1::PsLDH+URA3) strain, was removed in the same manner used in the URA3 pop-out. *Saccharomyces cerevisiae* CEN.PK2-1D (pdc1::PsLDH cyb2::PsLDH+URA3) was inoculated in about 10 ml of a YPD liquid medium and cultured for about 18 hours at a temperature of about 30° C., and then, the culture solution a 5-FOA (including YSD, 6.7 g/L of a yeast nitrogen base without amino acids, 1.4 g/L of an amino acid dropout mix, and 1 μg/L of 5-fluoroorotic acid) solid medium and cultured in a plate at a temperature of about 30° C. for about 24 hours or more. 10 colonies (a URA3 pop-out strain) formed in the plate were selected, transferred to another 5-FOA solid medium, and at the same time, cultured in a YSD liquid medium to separate genome DNA from the strain by using a commonly used kit (Gentra Puregene Cell kit, Qiagen, USA). In order to confirm URA3 pop-out, PCR was performed by using the separated genome DNA of the URA3 pop-out strain as a template and primers of SEQ ID NOS: 44 and 45, and then, electrophoresis was performed on the resulting PCR product. As a result, *Saccharomyces cerevisiae* CEN.PK2-1D (pdc1::PsLDH cyb2::PsLDH) was obtained.

A mutant strain, gpd1 deleted *Saccharomyces cerevisiae* CEN.PK2-1D (pdc1::PsLDH cyb2::PsLDH), was prepared in the same manner as follows. The resulting *Saccharomyces cerevisiae* CEN.PK2-1D (pdc1::PsLDH cyb2::PsLDH) was smeared was smeared on a YPD solid medium (10 g of a yeast extract, 20 g of peptone, 20 g of glucose) and cultured for about 24 hours at a temperature of about 30° C., and then a colony resulting from there was inoculated in about 10 ml of a YPD liquid medium for about 18 hours at a temperature of about 30° C. The sufficiently grown medium was inoculated in about 50 ml of a YPD liquid medium at a concentration of 1% (v/v) contained in a 250 ml-flask, and cultured in an incubator at a rate of about 230 rpm and a temperature of about 30° C. After about 4 to 5 hours, when $OD_{600}$ was about 0.5, the culture was centrifuged at a rate of about 4,500 rpm for about 10 minutes to obtain *Saccharomyces cerevisiae* cells, and the cells were resuspended in a lithium acetate solution at a concentration of about 100 mM. Then, the cells were centrifuged at a rate of about 4,500 rpm for about 10 minutes to obtain cells, resuspended in a lithium acetate solution at a concentration of about 1 M added with 15% of glycerol, and then divided into a volume of about 100 ul each.

In the same manner used in the PDC1 and CYB2 gene deletion, to remove CYB2 gene, to remove GPD1 gene, the GPD1 deletion cassette prepared in Example 1.2 was mixed with 50% of polyethyleneglycol and a single stranded carrier DNA and reacted in a water tub at a temperature of about 42° C. for about 1 hour, and then, the culture solution was smeared on a uracil-free minimal medium (including YSD, 6.7 g/L of yeast nitrogen base without amino acids, and 1.4 g/L of amino acid dropout mix (−ura)) in a plate and cultured at a temperature of about 30° C. for about 24 hours or more. 10 colonies (a mutant strain) formed in the plate were selected, transferred to another YSD (−ura) minimal solid medium, and at the same time, cultured in a YSD (−ura) liquid medium to separate genome DNA from the strain by using a commonly used kit (Gentra Puregene Cell kit, Qiagen, USA). In order to confirm gpd1 deletion, PCR was performed by using the separated genome DNA of the mutant strain as a template and primers of SEQ ID NOS: 46 and 47, and then, electrophoresis was performed on the resulting PCR product. As a result, *Saccharomyces cerevisiae* CEN.PK2-1D (pdc1::PsLDH cyb2::PsLDH gpd1::PsLDH+URA3) was obtained.

Also, for additional gene deletion by using the gene deletion vector, a selection marker, URA3 gene, used for gpd1 deletion was removed in the same manner used in the URA3 pop-out. *Saccharomyces cerevisiae* CEN.PK2-1D (pdc1::PsLDH cyb2::PsLDH gpd1::PsLDH+URA3) was inoculated in about 10 ml of a YPD liquid medium and cultured for about 18 hours at a temperature of about 30° C., and then, the culture solution a 5-FOA (including YSD, 6.7 g/L of a yeast nitrogen base without amino acids, 1.4 g/L of an amino acid dropout mix, and 1 μg/L of 5-fluoroorotic acid) solid medium and cultured in a plate at a temperature of about 30° C. for about 24 hours or more. 10 colonies (a URA3 pop-out strain) formed in the plate were selected, transferred to another 5-FOA solid medium, and at the same time, cultured in a YSD liquid medium to separate genome DNA from the strain by using a commonly used kit (Gentra Puregene Cell kit, Qiagen, USA). In order to confirm URA3 pop-out, PCR was performed by using the separated genome DNA of the URA3 pop-out strain as a template and primers of SEQ ID NOS: 46 and 47, and then, electrophoresis was performed on the resulting PCR product. As a result, *Saccharomyces cerevisiae* CEN.PK2-1D (pdc1::PsLDH cyb2::PsLDH gpd1::PsLDH) was obtained.

*Saccharomyces cerevisiae* CEN.PK2-1D (pdc1::PsLDH cyb2::PsLDH gpd1::PsLDH) was deposited in Korean Collection for Type Cultures (KCTC) on May 30, 2013, and received an Deposit number, KCTC 12415 BP.

Example 7

Preparation of Strain Prepared by Introducing L-LDH Overexpression Vector into KCTC12415BP+L-LDH Strain and Production of L-Lactate Using the Prepared Strain

(7.1) Preparation of Strain to which L-LDH Overexpression Vector Derived from *Sordaria macrospora* is Introduced The p416-CCW12-SmLDH plasmid prepared in Example 1 was inserted to the *Saccharomyces cerevisiae* CEN.PK2-1D (pdc1::PsLDH cyb2::PsLDH gpd1::PsLDH) strain prepared in Example 6 as follows.

The p416-CCW12-SmLDH plasmid prepared in Example 1 was mixed with 50% of polyethyleneglycol and a single stranded carrier DNA and reacted in a water tub at a temperature of about 42° C. for about 1 hour, and then, the culture solution was smeared on a uracil-free minimal medium (including YSD, 6.7 g/L of yeast nitrogen base without amino acids, and 1.4 g/L of amino acid dropout mix (−ura)) in a plate and cultured at a temperature of about 30° C. for about 24 hours or more.

8 colonies (a mutant strain) formed in the plate were selected, transferred to another YSD (−ura) minimal solid medium, and at the same time, cultured in a YSD (−ura) liquid medium to separate plasmid DNA from the strain by using a commonly used kit (Yeast plasmid isolation kit, Clontech). In order to confirm the plasmid included the Smldh gene, PCR was performed by using the separated plasmid DNA as a template and primers of SEQ ID NOS: 26 and 27, and then, electrophoresis was performed on the resulting PCR product to confirm that the plasmid is p416-CCW12-SmLDH. As a result, *Saccharomyces cerevisiae* CEN.PK2-1D (pdc1::PsLDH cyb2::PsLDH gpd1::PsLDH, +SmLDH) was obtained.

(7.2) Preparation of Strain to which L-LDH Overexpression Vector Derived from *Pelodiscus sinensis Japonicus* is Introduced The p416-CCW12p-LDH vector prepared in Example 6.1.1 was mixed with 50% of polyethyleneglycol and a single stranded carrier DNA and reacted in a water tub at a temperature of about 42° C. for about 1 hour, and then, the culture solution was smeared on a uracil-free minimal medium (including YSD, 6.7 g/L of yeast nitrogen base without amino acids, and 1.4 g/L of amino acid dropout mix (−ura)) in a plate and cultured at a temperature of about 30° C. for about 24 hours or more.

8 colonies (a mutant strain) formed in the plate were selected, transferred to another YSD (−ura) minimal solid medium, and at the same time, cultured in a YSD (−ura) liquid medium to separate plasmid DNA from the strain by using a commonly used kit (Yeast plasmid isolation kit, Clontech). In order to confirm the plasmid included the Psldh gene, PCR was performed by using the separated plasmid DNA as a template and primers of SEQ ID NOS: 29 and 30, and then, electrophoresis was performed on the resulting PCR product to confirm that the plasmid is p416-CCW12-PsLDH. As a result, *Saccharomyces cerevisiae* CEN.PK2-1D (pdc1::PsLDH cyb2::PsLDH gpd1::PsLDH, +PsLDH) was obtained.

(7.3) Lactate Production Using *Saccharomyces cerevisiae* Strain to which L-LDH Derived from *Sordaria macrospora* is Introduced After culturing and fermenting the strains prepared in Examples 7.1 and 7.2 in the same manner used in Example 5, samples were periodically collected from the flask during the fermentation, centrifuged at a rate of 13,000 rpm for about 10 minutes, and then the supernatant resulting from each of the samples was analyzed for concentrations of various metabolic products, lactate, and glycerol b using a high-pressure liquid chromatography (HPLC).

As shown in Table 2, the SmLDH overexpression vector-introduced KCTC12415BP strain had a better lactate productivity and an increased percent yield compared to the L-LDH (PsLDH) derived from *Pelodiscus sinensis japonicus*-introduced KCTC12415BP (control) strain. The lactate productivity and the percent yield of the SmLDH overexpression vector-introduced strain were respectively increased from about 15.31 g/L to about 15.62 g/L and from about 57.52% to about 58.40% compared to the PsLDH overexpression vector, which was the control group.

TABLE 2

| Vector introduced into KCTC12415BP | % yield (g/g) | Lactate (g/L) |
|---|---|---|
| SmLDH overexpression vector | 58.40 | 15.62 |
| PsLDH overexpression vector | 57.52 | 15.31 |
| KCTC12415BP (control) | 57.18 | 14.75 |

SmLDH: L-LDH derived from *Sordaria macrospora*
PsLDH: L-LDH derived from *Pelodiscus sinensis japonicus*
control: an empty vector

[Deposit Number]
Research Center Name: Korean Collection for Type Cultures (KTCT)
Deposit Number: KCTC 12443BP
Deposit Date Jul. 11, 2013

Research Center Name: Korean Collection for Type Cultures (KTCT)

Deposit Number: KCTC 12415BP

Deposit Date May 30, 2013

As described above, according to the one or more of the above embodiments of the present invention, a yeast cell may have lactate productivity, a vector may be used in a method of preparing the yeast cell having lactate productivity, and a method of producing lactate may efficiently produce lactate.

It should be understood that the exemplary embodiments described therein should be considered in a descriptive sense only and not for purposes of limitation. Descriptions of features or aspects within each embodiment should typically be considered as available for other similar features or aspects in other embodiments.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A recombinant yeast cell of the genus *Saccharomyces* comprising:

an exogenous gene encoding a lactate dehydrogenase (LDH) enzyme from a fungus of the genus *Sordaria* with the amino acid sequence of SEQ ID NO: 1; and a deletion or disruption mutation of a gene encoding a polypeptide that converts pyruvate into acetaldehyde.

2. The recombinant yeast cell of claim 1, wherein the recombinant yeast exhibits increased activity of converting pyruvate into lactate relative to a parent yeast cell not having LDH enzyme from *Sordaria* genus fungi.

3. The recombinant yeast cell of claim 1, wherein the exogenous gene encoding the LDH enzyme comprises SEQ ID NO: 2.

4. The recombinant yeast cell of claim 1, wherein the polypeptide that converts pyruvate into acetaldehyde has the amino acid sequence of SEQ ID NO: 3.

5. The recombinant yeast cell of claim 1, wherein the gene encoding polypeptide that converts pyruvate into acetaldehyde has the nucleotide sequence of SEQ ID NO: 4.

6. The recombinant yeast cell of claim 1, wherein the yeast cell is a yeast cell of Deposit No. KCTC 12443 BP deposited in the Korean Collection for Type Cultures.

7. The recombinant yeast cell of claim 1, wherein the recombinant yeast cell has a deletion or disruption mutation of a gene encoding a polypeptide that converts lactate into pyruvate, a gene encoding a polypeptide that converts dihydroxyacetone phosphate into glycerol-3-phosphate, or a combination thereof.

8. The recombinant yeast cell of claim 7, wherein the polypeptide that converts lactate into pyruvate and the polypeptide that converts dihydroxyacetone phosphate into glycerol-3-phosphate have the amino acid sequence of SEQ ID NOS: 5 and 7, respectively.

9. A method of producing lactate, the method comprising culturing the recombinant yeast cell of claim 1; and collecting lactate from the culture.

10. A method of preparing the recombinant yeast cell of claim 1 with improved lactase dehydrogenase activity, the method comprising introducing into the said yeast cell a gene encoding an LDH enzyme from *Sordaria* genus fungi with the amino acid sequence of SEQ ID NO: 1.

11. The method of claim 10, wherein the yeast cell comprising the gene encoding the LDH enzyme from a *Sordaria* genus fungi exhibits increased activity in converting pyruvate into lactate as compared to a parent yeast cell not having LDH enzyme from *Sordaria* genus fungi.

* * * * *

SEQUENCE LISTING

<160> NUMBER OF SEQ ID NOS: 47

<210> SEQ ID NO 1
<211> LENGTH: 324
<212> TYPE: PRT
<213> ORGANISM: Sordaria macrospora

<400> SEQUENCE: 1

```
Met Ser Val Pro Ser Thr Glu Ile Ser Ser His Ala Lys Ser Ile Lys
1               5                   10                  15

Val Val Ile Val Gly Ala Gly Ser Val Gly Val Thr Thr Ala Tyr Ala
            20                  25                  30

Leu Leu Leu Ser His Leu Ala Pro Glu Ile Val Leu Ile Asp Ile Asp
        35                  40                  45

Lys Asn Arg Ala Leu Gly Glu Ala Met Asp Leu Ser His Ala Ala His
    50                  55                  60

Tyr Ala His Ala Lys Val Ser Val Gly Asn Tyr Glu Asp Cys Ala Gly
65                  70                  75                  80

Ala Thr Ala Val Ile Ile Thr Ala Gly Val Asn Gln Lys Pro Gly Gln
                85                  90                  95

Thr Arg Met Asp Leu Val Lys Thr Asn Phe Gly Leu Phe Glu Lys Ile
            100                 105                 110

Val Pro Gln Ile Ala Lys His Ala Pro Asn Thr Ile Leu Ile Val Ala
        115                 120                 125

Thr Asn Pro Cys Asp Val Leu Thr Lys Ala Ala Gln Glu Leu Ser Gly
    130                 135                 140

Phe Pro Val Gln Arg Val Ile Gly Ser Gly Thr Ala Met Asp Thr Thr
145                 150                 155                 160

Arg Phe Arg His Glu Leu Gly Lys His Tyr Gly Val Asn Pro Arg Asn
                165                 170                 175

Val His Ala Val Ile Val Gly Glu His Gly Asp Ser Gln Leu Pro Val
            180                 185                 190

Trp Ser Leu Ala Thr Ile Ala Gly Met Arg Leu Glu Asp Tyr Cys Asn
        195                 200                 205

Gln Lys Gly Ile Ala Tyr Asp Glu Lys Ala Met Asp Ala Leu Gly Lys
    210                 215                 220

Arg Thr Arg Glu Ala Ala Tyr Glu Ile Ile Gln Arg Lys Gly Lys Thr
225                 230                 235                 240

Asn Tyr Gly Val Ala Ser Val Leu Val Ser Ile Leu Glu Pro Ile Ile
                245                 250                 255

Thr Asn Ala Asp Gln Leu Val Thr Val Ser Arg Val Gly Asn Tyr Ala
            260                 265                 270

Gly Val Glu Gly Val Ala Leu Ser Met Pro Cys Lys Leu Asn Ser Leu
        275                 280                 285

Gly Ala His Gln Asp Val Glu Leu Leu Leu Asn Asp Lys Glu Lys Glu
    290                 295                 300

Ala Leu Arg Lys Ser Ala Thr Ser Ile Lys Glu Cys Phe Asp Ser Val
305                 310                 315                 320

Ala Lys Lys Glu
```

<210> SEQ ID NO 2
<211> LENGTH: 975
<212> TYPE: DNA
<213> ORGANISM: Sordaria macrospora

<400> SEQUENCE: 2

-continued

```
atgagcgttc caagcacaga gatttcatct catgccaaat ctataaaggt tgtcatcgtt      60

ggtgcgggtt cagttggtgt cacaactgct tatgccttat tgctttcgca cttagcacca     120

gagatcgttc tgatcgacat tgataaaaat agagctttag gagaggcaat ggacctgtca     180

catgcagctc attacgctca cgcaaaagtt agtgttggaa actatgagga ttgtgctggg     240

gccacagcag ttatcataac agctggtgtt aaccaaaagc cagggcaaac taggatggat     300

ttagtcaaaa caaactttgg actatttgag aagatagtgc cccaaatagc taagcacgcg     360

cctaatacta ttttaatagt cgctaccaat ccctgtgatg tcttaacaaa agcggcacag     420

gagttatcag gattccctgt acagagagtt atcggttctg gaaccgctat ggatactacc     480

cgtttcagac acgaactggg caagcattat ggagtaaatc caagaaacgt acatgctgtg     540

attgtaggtg aacatggtga ttcccaacta cctgtatggt ccttagctac tattgctggt     600

atgcgtttgg aagattattg caatcaaaaa ggtatagcct acgatgaaaa agctatggat     660

gccttgggta aaagaactag ggaagcagca tacgaaatca ttcaaagaaa aggcaagacg     720

aattatggcg tggcatcggt ccttgtatct attttggaac cgattattac caatgcagac     780

caacttgtga ctgtctctag ggtgggcaat tacgccggtg tagaaggcgt ggctttaagt     840

atgccatgca aattgaacag tctaggtgcg catcaggacg ttgaattgtt gcttaacgac     900

aaggaaaaag aagccctacg taaatcagcc acgtccatta aagaatgttt tgattctgtt     960

gcaaagaagg aataa                                                      975


<210> SEQ ID NO 3
<211> LENGTH: 563
<212> TYPE: PRT
<213> ORGANISM: Saccharomyces cerevisiae

<400> SEQUENCE: 3

Met Ser Glu Ile Thr Leu Gly Lys Tyr Leu Phe Glu Arg Leu Lys Gln
1               5                   10                  15

Val Asn Val Asn Thr Val Phe Gly Leu Pro Gly Asp Phe Asn Leu Ser
            20                  25                  30

Leu Leu Asp Lys Ile Tyr Glu Val Glu Gly Met Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ser Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Ala Thr
    130                 135                 140

Ala Pro Ala Glu Ile Asp Arg Cys Ile Arg Thr Thr Tyr Val Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Gln Thr Pro Ile Asp Met Ser Leu Lys Pro Asn
            180                 185                 190
```

```
Asp Ala Glu Ser Glu Lys Glu Val Ile Asp Thr Ile Leu Ala Leu Val
        195                 200                 205

Lys Asp Ala Lys Asn Pro Val Ile Leu Ala Asp Ala Cys Cys Ser Arg
    210                 215                 220

His Asp Val Lys Ala Glu Thr Lys Lys Leu Ile Asp Leu Thr Gln Phe
225                 230                 235                 240

Pro Ala Phe Val Thr Pro Met Gly Lys Gly Ser Ile Asp Glu Gln His
                245                 250                 255

Pro Arg Tyr Gly Gly Val Tyr Val Gly Thr Leu Ser Lys Pro Glu Val
            260                 265                 270

Lys Glu Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys
    290                 295                 300

Asn Ile Val Glu Phe His Ser Asp His Met Lys Ile Arg Asn Ala Thr
305                 310                 315                 320

Phe Pro Gly Val Gln Met Lys Phe Val Leu Gln Lys Leu Leu Thr Asn
                325                 330                 335

Ile Ala Asp Ala Ala Lys Gly Tyr Lys Pro Val Ala Val Pro Ala Arg
            340                 345                 350

Thr Pro Ala Asn Ala Ala Val Pro Ala Ser Thr Pro Leu Lys Gln Glu
        355                 360                 365

Trp Met Trp Asn Gln Leu Gly Asn Phe Leu Gln Glu Gly Asp Val Val
    370                 375                 380

Ile Ala Glu Thr Gly Thr Ser Ala Phe Gly Ile Asn Gln Thr Thr Phe
385                 390                 395                 400

Pro Asn Asn Thr Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
            420                 425                 430

Asp Pro Lys Lys Arg Val Ile Leu Phe Ile Gly Asp Gly Ser Leu Gln
        435                 440                 445

Leu Thr Val Gln Glu Ile Ser Thr Met Ile Arg Trp Gly Leu Lys Pro
    450                 455                 460

Tyr Leu Phe Val Leu Asn Asn Asp Gly Tyr Thr Ile Glu Lys Leu Ile
465                 470                 475                 480

His Gly Pro Lys Ala Gln Tyr Asn Glu Ile Gln Gly Trp Asp His Leu
                485                 490                 495

Ser Leu Leu Pro Thr Phe Gly Ala Lys Asp Tyr Glu Thr His Arg Val
            500                 505                 510

Ala Thr Thr Gly Glu Trp Asp Lys Leu Thr Gln Asp Lys Ser Phe Asn
        515                 520                 525

Asp Asn Ser Lys Ile Arg Met Ile Glu Val Met Leu Pro Val Phe Asp
    530                 535                 540

Ala Pro Gln Asn Leu Val Glu Gln Ala Lys Leu Thr Ala Ala Thr Asn
545                 550                 555                 560

Ala Lys Gln
```

<210> SEQ ID NO 4
<211> LENGTH: 1692
<212> TYPE: DNA
<213> ORGANISM: Saccharomyces cerevisiae

<400> SEQUENCE: 4

```
atgtctgaaa ttactttggg taaatatttg ttcgaaagat taaagcaagt caacgttaac      60

accgttttcg gtttgccagg tgacttcaac ttgtccttgt tggacaagat ctacgaagtt     120

gaaggtatga gatgggctgg taacgccaac gaattgaacg ctgcttacgc cgctgatggt     180

tacgctcgta tcaagggtat gtcttgtatc atcaccacct tcggtgtcgg tgaattgtct     240

gctttgaacg gtattgccgg ttcttacgct gaacacgtcg gtgttttgca cgttgttggt     300

gtcccatcca tctcttctca agctaagcaa ttgttgttgc accacacctt gggtaacggt     360

gacttcactg ttttccacag aatgtctgcc aacatttctg aaaccactgc tatgatcact     420

gacattgcta ccgccccagc tgaaattgac agatgtatca gaaccactta cgtcacccaa     480

agaccagtct acttaggttt gccagctaac ttggtcgact tgaacgtccc agctaagttg     540

ttgcaaactc caattgacat gtctttgaag ccaaacgatg ctgaatccga aaaggaagtc     600

attgacacca tcttggcttt ggtcaaggat gctaagaacc cagttatctt ggctgatgct     660

tgttgttcca gacacgacgt caaggctgaa actaagaagt tgattgactt gactcaattc     720

ccagctttcg tcaccccaat gggtaagggt tccattgacg aacaacaccc aagatacggt     780

ggtgtttacg tcggtacctt gtccaagcca gaagttaagg aagccgttga atctgctgac     840

ttgattttgt ctgtcggtgc tttgttgtct gatttcaaca ccggttcttt ctcttactct     900

tacaagacca agaacattgt cgaattccac tccgaccaca tgaagatcag aaacgccact     960

ttcccaggtg tccaaatgaa attcgttttg caaaagttgt tgaccaatat tgctgacgcc    1020

gctaagggtt acaagccagt tgctgtccca gctagaactc cagctaacgc tgctgtccca    1080

gcttctaccc cattgaagca agaatggatg tggaaccaat tgggtaactt cttgcaagaa    1140

ggtgatgttg tcattgctga aaccggtacc tccgctttcg gtatcaacca aaccactttc    1200

ccaaacaaca cctacggtat ctctcaagtc ttatggggtt ccattggttt caccactggt    1260

gctaccttgg gtgctgcttt cgctgctgaa gaaattgatc caaagaagag agttatctta    1320

ttcattggtg acggttcttt gcaattgact gttcaagaaa tctccaccat gatcagatgg    1380

ggcttgaagc catacttgtt cgtcttgaac aacgatggtt acaccattga aaagttgatt    1440

cacggtccaa aggctcaata caacgaaatt caaggttggg accacctatc cttgttgcca    1500

actttcggtg ctaaggacta cgaaacccac agagtcgcta ccaccggtga atgggacaag    1560

ttgacccaag acaagtcttt caacgacaac tctaagatca gaatgattga ggttatgttg    1620

ccagtcttcg atgctccaca aaacttggtt gaacaagcta agttgactgc tgctaccaac    1680

gctaagcaat aa                                                        1692
```

<210> SEQ ID NO 5
<211> LENGTH: 591
<212> TYPE: PRT
<213> ORGANISM: Saccharomyces cerevisiae

<400> SEQUENCE: 5

```
Met Leu Lys Tyr Lys Pro Leu Leu Lys Ile Ser Lys Asn Cys Glu Ala
1               5                   10                  15

Ala Ile Leu Arg Ala Ser Lys Thr Arg Leu Asn Thr Ile Arg Ala Tyr
            20                  25                  30

Gly Ser Thr Val Pro Lys Ser Lys Ser Phe Glu Gln Asp Ser Arg Lys
        35                  40                  45

Arg Thr Gln Ser Trp Thr Ala Leu Arg Val Gly Ala Ile Leu Ala Ala
    50                  55                  60

Thr Ser Ser Val Ala Tyr Leu Asn Trp His Asn Gly Gln Ile Asp Asn
```

-continued

```
65                  70                  75                  80

Glu Pro Lys Leu Asp Met Asn Lys Gln Lys Ile Ser Pro Ala Glu Val
                85                  90                  95

Ala Lys His Asn Lys Pro Asp Asp Cys Trp Val Val Ile Asn Gly Tyr
            100                 105                 110

Val Tyr Asp Leu Thr Arg Phe Leu Pro Asn His Pro Gly Gly Gln Asp
        115                 120                 125

Val Ile Lys Phe Asn Ala Gly Lys Asp Val Thr Ala Ile Phe Glu Pro
    130                 135                 140

Leu His Ala Pro Asn Val Ile Asp Lys Tyr Ile Ala Pro Glu Lys Lys
145                 150                 155                 160

Leu Gly Pro Leu Gln Gly Ser Met Pro Pro Glu Leu Val Cys Pro Pro
                165                 170                 175

Tyr Ala Pro Gly Glu Thr Lys Glu Asp Ile Ala Arg Lys Glu Gln Leu
            180                 185                 190

Lys Ser Leu Leu Pro Pro Leu Asp Asn Ile Ile Asn Leu Tyr Asp Phe
        195                 200                 205

Glu Tyr Leu Ala Ser Gln Thr Leu Thr Lys Gln Ala Trp Ala Tyr Tyr
    210                 215                 220

Ser Ser Gly Ala Asn Asp Glu Val Thr His Arg Glu Asn His Asn Ala
225                 230                 235                 240

Tyr His Arg Ile Phe Phe Lys Pro Lys Ile Leu Val Asp Val Arg Lys
                245                 250                 255

Val Asp Ile Ser Thr Asp Met Leu Gly Ser His Val Asp Val Pro Phe
            260                 265                 270

Tyr Val Ser Ala Thr Ala Leu Cys Lys Leu Gly Asn Pro Leu Glu Gly
        275                 280                 285

Glu Lys Asp Val Ala Arg Gly Cys Gly Gln Gly Val Thr Lys Val Pro
    290                 295                 300

Gln Met Ile Ser Thr Leu Ala Ser Cys Ser Pro Glu Glu Ile Ile Glu
305                 310                 315                 320

Ala Ala Pro Ser Asp Lys Gln Ile Gln Trp Tyr Gln Leu Tyr Val Asn
                325                 330                 335

Ser Asp Arg Lys Ile Thr Asp Asp Leu Val Lys Asn Val Glu Lys Leu
            340                 345                 350

Gly Val Lys Ala Leu Phe Val Thr Val Asp Ala Pro Ser Leu Gly Gln
        355                 360                 365

Arg Glu Lys Asp Met Lys Leu Lys Phe Ser Asn Thr Lys Ala Gly Pro
    370                 375                 380

Lys Ala Met Lys Lys Thr Asn Val Glu Glu Ser Gln Gly Ala Ser Arg
385                 390                 395                 400

Ala Leu Ser Lys Phe Ile Asp Pro Ser Leu Thr Trp Lys Asp Ile Glu
                405                 410                 415

Glu Leu Lys Lys Lys Thr Lys Leu Pro Ile Val Ile Lys Gly Val Gln
            420                 425                 430

Arg Thr Glu Asp Val Ile Lys Ala Ala Glu Ile Gly Val Ser Gly Val
        435                 440                 445

Val Leu Ser Asn His Gly Gly Arg Gln Leu Asp Phe Ser Arg Ala Pro
    450                 455                 460

Ile Glu Val Leu Ala Glu Thr Met Pro Ile Leu Glu Gln Arg Asn Leu
465                 470                 475                 480

Lys Asp Lys Leu Glu Val Phe Val Asp Gly Gly Val Arg Arg Gly Thr
                485                 490                 495
```

```
Asp Val Leu Lys Ala Leu Cys Leu Gly Ala Lys Gly Val Gly Leu Gly
            500                 505                 510

Arg Pro Phe Leu Tyr Ala Asn Ser Cys Tyr Gly Arg Asn Gly Val Glu
        515                 520                 525

Lys Ala Ile Glu Ile Leu Arg Asp Glu Ile Glu Met Ser Met Arg Leu
    530                 535                 540

Leu Gly Val Thr Ser Ile Ala Glu Leu Lys Pro Asp Leu Leu Asp Leu
545                 550                 555                 560

Ser Thr Leu Lys Ala Arg Thr Val Gly Val Pro Asn Asp Val Leu Tyr
                565                 570                 575

Asn Glu Val Tyr Glu Gly Pro Thr Leu Thr Glu Phe Glu Asp Ala
            580                 585                 590


<210> SEQ ID NO 6
<211> LENGTH: 1776
<212> TYPE: DNA
<213> ORGANISM: Saccharomyces cerevisiae

<400> SEQUENCE: 6

atgctaaaat acaaaccttt actaaaaatc tcgaagaact gtgaggctgc tatcctcaga     60

gcgtctaaga ctagattgaa cacaatccgc gcgtacggtt ctaccgttcc aaaatccaag    120

tcgttcgaac aagactcaag aaaacgcaca cagtcatgga ctgccttgag agtcggtgca    180

attctagccg ctactagttc cgtggcgtat ctaaactggc ataatggcca aatagacaac    240

gagccgaaac tggatatgaa taaacaaaag atttcgcccg ctgaagttgc caagcataac    300

aagcccgatg attgttgggt tgtgatcaat ggttacgtat acgacttaac gcgattccta    360

ccaaatcatc caggtgggca ggatgttatc aagtttaacg ccgggaaaga tgtcactgct    420

atttttgaac cactacatgc tcctaatgtc atcgataagt atatagctcc cgagaaaaaa    480

ttgggtcccc ttcaaggatc catgcctcct gaacttgtct gtcctcctta tgctcctggt    540

gaaactaagg aagatatcgc tagaaaagaa caactaaaat cgctgctacc tcctctagat    600

aatattatta acctttacga ctttgaatac ttggcctctc aaactttgac taaacaagcg    660

tgggcctact attcctccgg tgctaacgac gaagttactc acagagaaaa ccataatgct    720

tatcatagga ttttttcaa accaaagatc cttgtagatg tacgcaaagt agacatttca     780

actgacatgt tgggttctca tgtggatgtt cccttctacg tgtctgctac agctttgtgt    840

aaactgggaa accccttaga aggtgaaaaa gatgtcgcca gaggttgtgg ccaaggtgtg    900

acaaaagtcc cacaaatgat atctactttg gcttcatgtt cccctgagga aattattgaa    960

gcagcaccct ctgataaaca aattcaatgg taccaactat atgttaactc tgatagaaag   1020

atcactgatg atttggttaa aaatgtagaa aagctgggtg taaaggcatt atttgtcact   1080

gtggatgctc caagtttagg tcaaagagaa aaagatatga agctgaaatt ttccaataca   1140

aaggctggtc caaaagcgat gaagaaaact aatgtagaag aatctcaagg tgcttcgaga   1200

gcgttatcaa agtttattga cccctctttg acttggaaag atatagaaga gttgaagaaa   1260

aagacaaaac tacctattgt tatcaaaggt gttcaacgta ccgaagatgt tatcaaagca   1320

gcagaaatcg gtgtaagtgg ggtggttcta tccaatcatg gtggtagaca attagatttt   1380

tcaagggctc ccattgaagt cctggctgaa accatgccaa tcctggaaca acgtaacttg   1440

aaggataagt tggaagtttt cgtggacggt ggtgttcgtc gtggtacaga tgtcttgaaa   1500

gcgttatgtc taggtgctaa aggtgttggt ttgggtagac cattcttgta tgcgaactca   1560
```

```
tgctatggtc gtaatggtgt tgaaaaagcc attgaaattt taagagatga aattgaaatg   1620

tctatgagac tattaggtgt tactagcatt gcggaattga agcctgatct tttagatcta   1680

tcaacactaa aggcaagaac agttggagta ccaaacgacg tgctgtataa tgaagtttat   1740

gagggaccta ctttaacaga atttgaggat gcatga                              1776


<210> SEQ ID NO 7
<211> LENGTH: 391
<212> TYPE: PRT
<213> ORGANISM: Saccharomyces cerevisiae

<400> SEQUENCE: 7

Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335
```

```
Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390


<210> SEQ ID NO 8
<211> LENGTH: 1176
<212> TYPE: DNA
<213> ORGANISM: Saccharomyces cerevisiae

<400> SEQUENCE: 8

atgtctgctg ctgctgatag attaaactta acttccggcc acttgaatgc tggtagaaag      60

agaagttcct cttctgtttc tttgaaggct gccgaaaagc ctttcaaggt tactgtgatt     120

ggatctggta actggggtac tactattgcc aaggtggttg ccgaaaattg taagggatac     180

ccagaagttt tcgctccaat agtacaaatg tgggtgttcg aagaagagat caatggtgaa     240

aaattgactg aaatcataaa tactagacat caaaacgtga aatacttgcc tggcatcact     300

ctacccgaca atttggttgc taatccagac ttgattgatt cagtcaagga tgtcgacatc     360

atcgttttca acattccaca tcaatttttg ccccgtatct gtagccaatt gaaaggtcat     420

gttgattcac acgtcagagc tatctcctgt ctaaagggtt ttgaagttgg tgctaaaggt     480

gtccaattgc tatcctctta catcactgag gaactaggta ttcaatgtgg tgctctatct     540

ggtgctaaca ttgccaccga agtcgctcaa gaacactggt ctgaaacaac agttgcttac     600

cacattccaa aggatttcag aggcgagggc aaggacgtcg accataaggt tctaaaggcc     660

ttgttccaca gaccttactt ccacgttagt gtcatcgaag atgttgctgg tatctccatc     720

tgtggtgctt tgaagaacgt tgttgcctta ggttgtggtt tcgtcgaagg tctaggctgg     780

ggtaacaacg cttctgctgc catccaaaga gtcggtttgg gtgagatcat cagattcggt     840

caaatgtttt tcccagaatc tagagaagaa acatactacc aagagtctgc tggtgttgct     900

gatttgatca ccacctgcgc tggtggtaga aacgtcaagg ttgctaggct aatggctact     960

tctggtaagg acgcctggga atgtgaaaag gagttgttga atggccaatc cgctcaaggt    1020

ttaattacct gcaaagaagt tcacgaatgg ttggaaacat gtggctctgt cgaagacttc    1080

ccattatttg aagccgtata ccaaatcgtt tacaacaact acccaatgaa gaacctgccg    1140

gacatgattg aagaattaga tctacatgaa gattag                              1176


<210> SEQ ID NO 9
<211> LENGTH: 289
<212> TYPE: DNA
<213> ORGANISM: Artificial Sequence
<220> FEATURE:
<223> OTHER INFORMATION: Synthetic (CYC promoter)

<400> SEQUENCE: 9

atttggcgag cgttggttgg tggatcaagc ccacgcgtag gcaatcctcg agcagatccg      60

ccaggcgtgt atatatagcg tggatggcca ggcaacttta gtgctgacac atacaggcat     120

atatatatgt gtgcgacgac acatgatcat atggcatgca tgtgctctgt atgtatataa     180

aactcttgtt ttcttctttt ctctaaatat tctttcctta tacattagga cctttgcagc     240

ataaattact atacttctat agacacgcaa acacaaatac acacactaa                 289
```

<210> SEQ ID NO 10
<211> LENGTH: 401
<212> TYPE: DNA
<213> ORGANISM: Artificial Sequence
<220> FEATURE:
<223> OTHER INFORMATION: Synthetic (TEF promoter)

<400> SEQUENCE: 10
atagcttcaa aatgtttcta ctcctttttt actcttccag attttctcgg actccgcgca 60
tcgccgtacc acttcaaaac acccaagcac agcatactaa atttcccctc tttcttcctc 120
tagggtgtcg ttaattaccc gtactaaagg tttggaaaag aaaaaagaga ccgcctcgtt 180
tctttttctt cgtcgaaaaa ggcaataaaa atttttatca cgtttctttt tcttgaaaat 240
tttttttttg atttttttct ctttcgatga cctcccattg atatttaagt taataaacgg 300
tcttcaattt ctcaagtttc agtttcattt ttcttgttct attacaactt tttttacttc 360
ttgctcatta gaaagaaagc atagcaatct aatctaagtt t 401

<210> SEQ ID NO 11
<211> LENGTH: 655
<212> TYPE: DNA
<213> ORGANISM: Artificial Sequence
<220> FEATURE:
<223> OTHER INFORMATION: Synthetic (GPD promoter)

<400> SEQUENCE: 11
agtttatcat tatcaatact cgccatttca aagaatacgt aaataattaa tagtagtgat 60
tttcctaact ttatttagtc aaaaaattag ccttttaatt ctgctgtaac ccgtacatgc 120
ccaaaatagg gggcgggtta cacagaatat ataacatcgt aggtgtctgg gtgaacagtt 180
tattcctggc atccactaaa tataatggag cccgcttttt aagctggcat ccagaaaaaa 240
aaagaatccc agcaccaaaa tattgttttc ttcaccaacc atcagttcat aggtccattc 300
tcttagcgca actacagaga acaggggcac aaacaggcaa aaaacgggca caacctcaat 360
ggagtgatgc aacctgcctg gagtaaatga tgacacaagg caattgaccc acgcatgtat 420
ctatctcatt ttcttacacc ttctattacc ttctgctctc tctgatttgg aaaaagctga 480
aaaaaaaggt tgaaaccagt tccctgaaat tattccccta cttgactaat aagtatataa 540
agacggtagg tattgattgt aattctgtaa atctatttct taaacttctt aaattctact 600
tttatagtta gtcttttttt tagttttaaa acaccagaac ttagtttcga cggat 655

<210> SEQ ID NO 12
<211> LENGTH: 1468
<212> TYPE: DNA
<213> ORGANISM: Artificial Sequence
<220> FEATURE:
<223> OTHER INFORMATION: Synthetic (ADH promoter)

<400> SEQUENCE: 12
gccgggatcg aagaaatgat ggtaaatgaa ataggaaatc aaggagcatg aaggcaaaag 60
acaaatataa gggtcgaacg aaaaataaag tgaaaagtgt tgatatgatg tatttggctt 120
tgcggcgccg aaaaaacgag tttacgcaat tgcacaatca tgctgactct gtggcggacc 180
cgcgctcttg ccggcccggc gataacgctg ggcgtgaggc tgtgcccggc ggagtttttt 240
gcgcctgcat tttccaaggt ttaccctgcg ctaaggggcg agattggaga agcaataaga 300
atgccggttg gggttgcgat gatgacgacc acgacaactg gtgtcattat ttaagttgcc 360
gaaagaacct gagtgcattt gcaacatgag tatactagaa gaatgagcca agacttgcga 420
gacgcgagtt tgccggtggt gcgaacaata gagcgaccat gaccttgaag gtgagacgcg 480
cataaccgct agagtacttt gaagaggaaa cagcaatagg gttgctacca gtataaatag 540
acaggtacat acaacactgg aaatggttgt ctgtttgagt acgctttcaa ttcatttggg 600
tgtgcacttt attatgttac aatatggaag ggaactttac acttctccta tgcacatata 660
ttaattaaag tccaatgcta gtagagaagg ggggtaacac ccctccgcgc tcttttccga 720
tttttttcta aaccgtggaa tatttcggat atccttttgt tgtttccggg tgtacaatat 780
ggacttcctc ttttctggca accaaaccca tacatcggga ttcctataat accttcgttg 840
gtctccctaa catgtaggtg gcggagggga gatatacaat agaacagata ccagacaaga 900
cataatgggc taaacaagac tacaccaatt acactgcctc attgatggtg gtacataacg 960
aactaatact gtagccctag acttgatagc catcatcata tcgaagtttc actacccttt 1020
ttccatttgc catctattga agtaataata ggcgcatgca acttcttttc ttttttttc 1080 ttttctctct cccccgttgt tgtctcacca tatccgcaat gacaaaaaaa tgatggaaga 1140
cactaaagga aaaaattaac gacaaagaca gcaccaacag atgtcgttgt tccagagctg 1200
atgaggggta tctcgaagca cacgaaactt tttccttcct tcattcacgc acactactct 1260
ctaatgagca acggtatacg gccttccttc cagttacttg aatttgaaat aaaaaaaagt 1320
ttgctgtctt gctatcaagt ataaatagac ctgcaattat taatcttttg tttcctcgtc 1380
attgttctcg ttccctttct tccttgtttc tttttctgca caatatttca agctatacca 1440
agcatacaat caactccaag ctggccgc 1468

<210> SEQ ID NO 13
<211> LENGTH: 252
<212> TYPE: DNA
<213> ORGANISM: Artificial Sequence
<220> FEATURE:
<223> OTHER INFORMATION: Synthetic (CYC1 terminator)

<400> SEQUENCE: 13
tcatgtaatt agttatgtca cgcttacatt cacgccctcc ccccacatcc gctctaaccg 60
aaaaggaagg agttagacaa cctgaagtct aggtccctat ttattttttt atagttatgt 120
tagtattaag aacgttattt atatttcaaa tttttctttt ttttctgtac agacgcgtgt 180
acgcatgtaa cattatactg aaaaccttgc ttgagaaggt tttgggacgc tcgaaggctt 240
taatttgcgg cc 252

<210> SEQ ID NO 14
<211> LENGTH: 31
<212> TYPE: DNA
<213> ORGANISM: Artificial Sequence
<220> FEATURE:
<223> OTHER INFORMATION: Synthetic (forward primer)

<400> SEQUENCE: 14
cgagctcttc gcggccacct acgccgctat c 31

<210> SEQ ID NO 15
<211> LENGTH: 32
<212> TYPE: DNA
<213> ORGANISM: Artificial Sequence
<220> FEATURE:
<223> OTHER INFORMATION: Synthetic (reverse primer)

<400> SEQUENCE: 15
gctctagata ttgatatagt gtttaagcga at 32

<210> SEQ ID NO 16
<211> LENGTH: 40
<212> TYPE: DNA
<213> ORGANISM: Artificial Sequence
<220> FEATURE:
<223> OTHER INFORMATION: Synthetic (forward primer)

<400> SEQUENCE: 16
gcggccgcga attcggatcc gtagatacat tgatgctatc 40

<210> SEQ ID NO 17
<211> LENGTH: 29
<212> TYPE: DNA
<213> ORGANISM: Artificial Sequence
<220> FEATURE:
<223> OTHER INFORMATION: Synthetic (reverse primer)

<400> SEQUENCE: 17
gcggccgctc cgcggctcgt gctatattc 29

<210> SEQ ID NO 18
<211> LENGTH: 23
<212> TYPE: DNA
<213> ORGANISM: Artificial Sequence
<220> FEATURE:
<223> OTHER INFORMATION: Synthetic (forward primer)

<400> SEQUENCE: 18
gaattcaaca agctcatgca aag 23

<210> SEQ ID NO 19
<211> LENGTH: 27
<212> TYPE: DNA
<213> ORGANISM: Artificial Sequence
<220> FEATURE:
<223> OTHER INFORMATION: Synthetic (reverse primer)

<400> SEQUENCE: 19
gaattcctcg aggatttgac tgtgtta 27

<210> SEQ ID NO 20
<211> LENGTH: 26
<212> TYPE: DNA
<213> ORGANISM: Artificial Sequence
<220> FEATURE:
<223> OTHER INFORMATION: Synthetic (forward primer)

<400> SEQUENCE: 20
ccgctcgaga tgattgaaca agatgg 26

<210> SEQ ID NO 21
<211> LENGTH: 27
<212> TYPE: DNA
<213> ORGANISM: Artificial Sequence
<220> FEATURE:
<223> OTHER INFORMATION: Synthetic (reverse primer)

<400> SEQUENCE: 21
cgcggatcct cagaagaact cgtcaag 27

<210> SEQ ID NO 22
<211> LENGTH: 60
<212> TYPE: DNA

<213> ORGANISM: Artificial Sequence
<220> FEATURE:
<223> OTHER INFORMATION: Synthetic (forward primer)

<400> SEQUENCE: 22
aagatctacg aagttgaagg tatgagatgg gctggtaacg taatacgact cactataggg 60

<210> SEQ ID NO 23
<211> LENGTH: 61
<212> TYPE: DNA
<213> ORGANISM: Artificial Sequence
<220> FEATURE:
<223> OTHER INFORMATION: Synthetic (reverse primer)

<400> SEQUENCE: 23
gcttccttaa cttctggctt ggacaaggta ccgacgtaaa aacaagctca tgcaaagagg 60
t 61

<210> SEQ ID NO 24
<211> LENGTH: 22
<212> TYPE: DNA
<213> ORGANISM: Artificial Sequence
<220> FEATURE:
<223> OTHER INFORMATION: Synthetic (forward primer)

<400> SEQUENCE: 24
gctcttctct accctgtcat tc 22

<210> SEQ ID NO 25
<211> LENGTH: 22
<212> TYPE: DNA
<213> ORGANISM: Artificial Sequence
<220> FEATURE:
<223> OTHER INFORMATION: Synthetic (reverse primer)

<400> SEQUENCE: 25
tagtgtacag ggtgtcgtat ct 22

<210> SEQ ID NO 26
<211> LENGTH: 15
<212> TYPE: DNA
<213> ORGANISM: Artificial Sequence
<220> FEATURE:
<223> OTHER INFORMATION: Synthetic (forward primer)

<400> SEQUENCE: 26
ttcgcggcca cctac 15

<210> SEQ ID NO 27
<211> LENGTH: 21
<212> TYPE: DNA
<213> ORGANISM: Artificial Sequence
<220> FEATURE:
<223> OTHER INFORMATION: Synthetic (reverse primer)

<400> SEQUENCE: 27
caaattaaag ccttcgagcg t 21

<210> SEQ ID NO 28
<211> LENGTH: 999
<212> TYPE: DNA
<213> ORGANISM: Pelodiscus sinensis japonicus

<400> SEQUENCE: 28
atgtccgtaa aggaactact tatacaaaac gtccataagg aggagcattc tcacgctcac 60
aataagataa cagttgtagg agtaggtgca gtaggtatgg catgtgctat ttcgatatta 120
atgaaagact tggctgatga actagccttg gttgatgtga ttgaggataa gttacgtgga 180
gaaatgttag atttgcaaca tggttcattg ttcttgagaa cccccaaaat tgtctcgggt 240
aaggattatt cagtcactgc tcattctaaa ctggttatca ttacagcagg tgcaagacag 300
caagaagggg agagcagact aaatctggtt caacgtaatg tcaacatctt caagtttatc 360
atcccgaacg tagtaaaata cagtccagac tgcatgttgc ttgttgtgag taatccagtt 420
gacatcttaa cctatgttgc gtggaaaatc agtgggtttc caaaacatag ggtgattggc 480
tcaggatgca accttgatag cgccaggttt aggtatctaa tgggagaaaa attaggtatt 540
cactccttat cttgtcatgg ctggataata ggcgaacatg gtgattcttc ggtacctgtt 600
tggtccgggg ttaatgtggc tggtgttagt ttaaaagcat tatatcctga cctgggtact 660
gatgccgata aagaacattg gaaagaagtg cacaaacaag tggttgattc tgcttacgaa 720
gttattaaac ttaagggcta cacttcttgg gctataggtc tatcagtagc tgatttggca 780
gaaaccgtta tgaaaaattt aagaagagtc cacccaattt ccacgatggt caagggtatg 840
tacggtgtta gctctgacgt cttcttatct gttccttgtg ttttgggata tgcgggaatt 900
acagacgtcg tgaagatgac attgaaatca gaggaagagg aaaaactaag aaagtcagcc 960
gatactctgt ggggcattca aaaggaattg cagttttaa 999

<210> SEQ ID NO 29
<211> LENGTH: 26
<212> TYPE: DNA
<213> ORGANISM: Artificial Sequence
<220> FEATURE:
<223> OTHER INFORMATION: Synthetic (forward primer)

<400> SEQUENCE: 29
ggatccatgt ccgtaaagga actact 26

<210> SEQ ID NO 30
<211> LENGTH: 34
<212> TYPE: DNA
<213> ORGANISM: Artificial Sequence
<220> FEATURE:
<223> OTHER INFORMATION: Synthetic (reverse primer)

<400> SEQUENCE: 30
acgcgtcgac ttaaaactgc aattcctttt gaat 34

<210> SEQ ID NO 31
<211> LENGTH: 1267
<212> TYPE: DNA
<213> ORGANISM: Artificial Sequence
<220> FEATURE:
<223> OTHER INFORMATION: Synthetic (ARS/CEN)

<400> SEQUENCE: 31
gagctccttt catttctgat aaaagtaaga ttactccatt tatcttttca ccaacatatt 60
catagttgaa agttatcctt ctaagtacgt atacaatatt aattaaacgt aaaaacaaaa 120
ctgactgtaa aaatgtgtaa aaaaaaaata tcaaattcat agcagtttca aggaatgaaa 180
actattatga tctggtcacg tgtatataaa ttattaattt taaacccata taatttatta 240
tttttttatt ctaaagttta aagtaatttt agtagtattt tatattttga ataaatatac 300
tttaaatttt tatttttata ttttattact tttaaaaata atgtttttat ttaaaacaaa 360

```
attataagtt aaaaagttgt tccgaaagta aaatatattt tatagttttt acaaaaataa    420

attattttta acgtattttt tttaattata tttttgtatg tgattatatc cacaggtatt    480

atgctgaatt tagctgtttc agtttaccag tgtgatagta tgattttttt tgcctctcaa    540

aagctatttt tttagaagct tcgtcttaga aataggtggt gtataaattg cggttgactt    600

ttaactatat atcattttcg atttatttat tacatagaga ggtgctttta atttttttaat   660

ttttattttc aataatttta aaagtgggta cttttaaatt ggaacaaagt gaaaaatatc    720

tgttatacgt gcaactgaat tttactgacc ttaaaggact atctcaatcc tggttcagaa    780

atccttgaaa tgattgatat gttggtggat tttctctgat tttcaaacaa gaggtatttt    840

atttcatatt tattatattt tttacattta ttttatattt ttttattgtt tggaagggaa    900

agcgacaatc aaattcaaaa tatattaatt aaactgtaat acttaataag agacaaataa    960

cagccaagaa tcaaatactg ggtttttaat caaaagatct ctctacatgc acccaaattc   1020

attatttaaa tttactatac tacagacaga atatacgaac ccagattaag tagtcagacg   1080

cttttccgct ttattgagta tatagcctta catattttct gcccataatt tctggattta   1140

aaataaacaa aaatggttac tttgtagtta tgaaaaaagg cttttccaaa atgcgaaata   1200

cgtgttattt aaggttaatc aacaaaacgc atatccatat gggtagttgg acaaaacttc   1260

aatcgat                                                             1267
```

<210> SEQ ID NO 32
<211> LENGTH: 31
<212> TYPE: DNA
<213> ORGANISM: Artificial Sequence
<220> FEATURE:
<223> OTHER INFORMATION: Synthetic (forward primer)

<400> SEQUENCE: 32

```
cgagctcttc gcggccacct acgccgctat c                                    31
```

<210> SEQ ID NO 33
<211> LENGTH: 32
<212> TYPE: DNA
<213> ORGANISM: Artificial Sequence
<220> FEATURE:
<223> OTHER INFORMATION: Synthetic (reverse primer)

<400> SEQUENCE: 33

```
gctctagata ttgatatagt gtttaagcga at                                   32
```

<210> SEQ ID NO 34
<211> LENGTH: 26
<212> TYPE: DNA
<213> ORGANISM: Artificial Sequence
<220> FEATURE:
<223> OTHER INFORMATION: Synthetic (forward primer)

<400> SEQUENCE: 34

```
gagctcaatt aaccctcact aaaggg                                          26
```

<210> SEQ ID NO 35
<211> LENGTH: 26
<212> TYPE: DNA
<213> ORGANISM: Artificial Sequence
<220> FEATURE:
<223> OTHER INFORMATION: Synthetic (reverse primer)

<400> SEQUENCE: 35

```
gagctccaaa ttaaagcctt cgagcg                                          26
```

<210> SEQ ID NO 36
<211> LENGTH: 60
<212> TYPE: DNA
<213> ORGANISM: Artificial Sequence
<220> FEATURE:
<223> OTHER INFORMATION: Synthetic (forward primer)

<400> SEQUENCE: 36
aagatctacg aagttgaagg tatgagatgg gctggtaacg ccagtcacga cgttgtaaaa 60

<210> SEQ ID NO 37
<211> LENGTH: 60
<212> TYPE: DNA
<213> ORGANISM: Artificial Sequence
<220> FEATURE:
<223> OTHER INFORMATION: Synthetic (reverse primer)

<400> SEQUENCE: 37
gcttccttaa cttctggctt ggacaaggta ccgacgtaaa aggtttcccg actggaaagc 60

<210> SEQ ID NO 38
<211> LENGTH: 70
<212> TYPE: DNA
<213> ORGANISM: Artificial Sequence
<220> FEATURE:
<223> OTHER INFORMATION: Synthetic (forward primer)

<400> SEQUENCE: 38
cgatgcgtat tttaagtggt tctctgaaca gcacaatgtc ctcgacacca ccagtcacga 60
cgttgtaaaa 70

<210> SEQ ID NO 39
<211> LENGTH: 72
<212> TYPE: DNA
<213> ORGANISM: Artificial Sequence
<220> FEATURE:
<223> OTHER INFORMATION: Synthetic (reverse primer)

<400> SEQUENCE: 39
ggatcacccc ccactcaagt cgttgcattg ctaacatgtg gcattctgcc caaggtttcc 60
cgactggaaa gc 72

<210> SEQ ID NO 40
<211> LENGTH: 70
<212> TYPE: DNA
<213> ORGANISM: Artificial Sequence
<220> FEATURE:
<223> OTHER INFORMATION: Synthetic (forward primer)

<400> SEQUENCE: 40
ccctatgtct ctggccgatc acgcgccatt gtccctcaga aacaaatcaa ccagtcacga 60
cgttgtaaaa 70

<210> SEQ ID NO 41
<211> LENGTH: 70
<212> TYPE: DNA
<213> ORGANISM: Artificial Sequence
<220> FEATURE:
<223> OTHER INFORMATION: Synthetic (reverse primer)

<400> SEQUENCE: 41
tagaagcaac tgtgccgaca gcctctgaat gagtggtgtt gtaaccaccc aggtttcccg 60

```
actggaaagc                                                        70


<210> SEQ ID NO 42
<211> LENGTH: 22
<212> TYPE: DNA
<213> ORGANISM: Artificial Sequence
<220> FEATURE:
<223> OTHER INFORMATION: Synthetic (forward primer)

<400> SEQUENCE: 42

gctcttctct accctgtcat tc                                          22


<210> SEQ ID NO 43
<211> LENGTH: 22
<212> TYPE: DNA
<213> ORGANISM: Artificial Sequence
<220> FEATURE:
<223> OTHER INFORMATION: Synthetic (reverse primer)

<400> SEQUENCE: 43

tagtgtacag ggtgtcgtat ct                                          22


<210> SEQ ID NO 44
<211> LENGTH: 26
<212> TYPE: DNA
<213> ORGANISM: Artificial Sequence
<220> FEATURE:
<223> OTHER INFORMATION: Synthetic (forward primer)

<400> SEQUENCE: 44

ggagttgaag gcaaaattag aagtga                                      26


<210> SEQ ID NO 45
<211> LENGTH: 26
<212> TYPE: DNA
<213> ORGANISM: Artificial Sequence
<220> FEATURE:
<223> OTHER INFORMATION: Synthetic (reverse primer)

<400> SEQUENCE: 45

attccctttc ctgcacaaca cgagat                                      26


<210> SEQ ID NO 46
<211> LENGTH: 25
<212> TYPE: DNA
<213> ORGANISM: Artificial Sequence
<220> FEATURE:
<223> OTHER INFORMATION: Synthetic (forward primer)

<400> SEQUENCE: 46

tcaatgagac tgttgtcctc ctact                                       25


<210> SEQ ID NO 47
<211> LENGTH: 24
<212> TYPE: DNA
<213> ORGANISM: Artificial Sequence
<220> FEATURE:
<223> OTHER INFORMATION: Synthetic (reverse primer)

<400> SEQUENCE: 47

tacatccttg tcgagccttg ggca                                        24
```